(12) United States Patent
O'Mahony et al.

(10) Patent No.: US 6,699,973 B1
(45) Date of Patent: Mar. 2, 2004

(54) ANTIBODIES TO PEPTIDES THAT TARGET GIT RECEPTORS AND RELATED METHODS

(75) Inventors: Daniel Joseph O'Mahony, Blackrock (IE); Michela Seveso, Padua (IT)

(73) Assignee: Elan Corporation, PLC, Dublin (IE)

( * ) Notice: Subject to any disclaimer, the term of this patent is extended or adjusted under 35 U.S.C. 154(b) by 0 days.

(21) Appl. No.: 09/443,780

(22) Filed: Nov. 19, 1999

Related U.S. Application Data
(60) Provisional application No. 60/109,036, filed on Nov. 19, 1998.

(51) Int. Cl.$^7$ ............................................. C07K 16/00
(52) U.S. Cl. ................. 530/387.9; 530/388.1; 530/388.24; 530/389.2; 424/139.1; 424/133.1; 424/135.1; 424/141.1; 424/145.1; 424/158.1; 424/152.1
(58) Field of Search ............................ 530/388.1, 387.1, 530/388.22, 387.9, 388.24, 389.2; 435/7.1; 424/130.1, 135.1, 139.1, 141.1, 143.1, 152.1, 133.1, 145.1, 158.1

(56) References Cited

FOREIGN PATENT DOCUMENTS
WO 98/51325 11/1998

OTHER PUBLICATIONS

Lobie et al., Journal of Endocrinology (Dec. 1993) 139 (2) 371–82.*

Lobie et al., Endocrinology, (1990) 126(1), 299–306.*

Bertran et al., "Expression Cloning of a Human Renal cDNA That Induces High Affinity Transport of L–Cystine Shared with Dibasic Amino Acids in Xenopus Oocytes," J. Biol. Chem., 268(20):14842–14949 (1993).

Chantret et al., "Sequence of the complete cDNA and the 5' structure of the human sucrase–isomaltase gene," Biochem. J., 285:915–923 (1992).

Dantzig et al., "Association of Intestinal Peptide Transport with a Protein Related to the Cadherin Superfamily," Science, 264(5157):430–433 (1994).

Hochuli, E., "Purification of Recombinant Proteins with Metal Chelate Absorbent", Genetic Engineering, Principals and Methods, Setlow, ed., Plenum Press, NY, 12:87–98 (1990).

Liang et al., "Human Intestinal H+/Peptide Cotransporter," J. Biol. Chem., 270(12):6456–6463 (1995).

Lobie et al., "Growth Hormone Receptor Expression in the Rat Gastrointestinal Tract," Endocrinology, 126(1):299–306 (1990).

Lobie et al., "Prolactin receptor expression in the gastrointestinal tract: characterization of the prolactin receptor of gastric mucosa," J Endocrinology, 139(3):371–382 (1993).

* cited by examiner

*Primary Examiner*—Laurie Scheiner

(57) ABSTRACT

The invention provides an antibody or antibody fragment specific to a domain of a GIT targeting agent, such as a polyclonal antibody, monoclonal antibody, chimeric antibody, single chain antibody, a Fab fragment or a Fab expression library. In particular, the invention provides an antibody or antibody fragment, wherein the GIT targeting agent is selected from the group consisting of ZElan033 (PAX2 15 mer), ZElan088 (HAX42-2 20 mer) or ZElan053 (P31 D-form 16 mer). Numerous methods using these GIT targeting agent specific antibodies are disclosed.

2 Claims, 5 Drawing Sheets

| peptide | Description | Sequence |
|---|---|---|
| ZElan018 | PAX2 | STPPSREAYSRPYSVDSDSDTNAKHSSHNRRLRTRSRPNG |
| ZElan104 | PAX2 15mer cyclic (internal) | TNAKHSSCNRRLRCR |
| Unconj. Ag | PAX2 15mer (= Zelan033) | TNAKHSSHNRRLRTR |
| ZElan103A | PAX2 15mer cyclic (internal) | TNAKHSSCNRRCRTR |

| peptide | Description | Sequence |
|---|---|---|
| ZElan024 | P31 | SARDSGPAEDGSRAVRLNGVENANTRKSSRSNPRGRRHPGG |
| Unconj. Ag | P31 16mer Dform (= ZElan053) | TrKSSrSNPrGrrHPG |
| ZElan054 | P31 16mer Dform | TRKSSrSNPRGrRHPG |
| ZElan145 | P31 16mer Dform retroinversion | gphrrgrpnsrsskrt |

ANTIBODIES TO PEPTIDES THAT TARGET GIT RECEPTORS AND RELATED METHODS

This Application claims the benefits of a Provisional Application No. 60/109,036 filed Nov. 19, 1998.

FIELD OF THE INVENTION

The present invention relates to antibodies to random peptides capable of targeting or specifically binding to gastrointestinal tract (GIT) transport receptors. In particular, this invention relates to methods of using these antibodies as well as specific antibody preparations directed to particular GIT random peptide targeting agents.

BACKGROUND OF THE INVENTION

Antibodies can be produced by using an immunogen to generate antibodies which immunospecifically bind such an immunogen. Such antibodies include but are not limited to polyclonal, monoclonal, chimeric, single chain, Fab fragments, and an Fab expression library.

Various procedures known in the art may be useful for the production of polyclonal antibodies to an immunogen. For the production of antibody, various host animals, such as rabbits, mice, rats, fowl etc. can be immunized by injection with the immunogen. Various adjuvants may be used to increase the immunological response, depending on the host species, such as Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

As disclosed and claimed in WO 98/51325, which reference is hereby incorporated by reference in its entirety, we have identified random peptides and their fragments, motifs, derivatives, analogs or peptidomimetics thereof which are capable of specific binding to GIT transport receptors such as the D2H, hSI, HPT1 and hPEPT1 receptors (hereinafter referred to as "GIT targeting agents"). These GIT targeting agents are capable of facilitating transport of an active agent through a human or animal gastro-intestinal tissue and have use, for example, in facilitating transport of active agents from the lumenal side of the GIT into the portal, hepatic or systemic blood system and/or in targeting active agents to the GIT. Thus, for example, by binding (covalently or noncovalently) the GIT targeting agent to an orally administered active agent, the active agent can be targeted to specific receptor sites or transport pathways which are known to operate in the human gastrointestinal tract, thus facilitating its absorption into the systemic system. Preferably, the active agent is a drug or a drug-containing nano- or microparticle. Preferably, the tissue through which transport is facilitated is of the duodenum, jejunum, ileum, ascending colon, transverse colon, descending colon, or pelvic colon. The tissue is most preferably epithelial cells lining the lumenal side of the GIT.

The GIT targeting agents are bound to a material comprising an active agent. Such compositions have use in targeting the active agent to the GIT and/or in facilitating transfer through the lumen of the GIT into the systemic circulation. Where the active agent is an imaging agent, such compositions can be administered in vivo to image the GIT (or particular transport receptors thereof). Other active agents include but are not limited to: any drug or antigen or any drug- or antigen-loaded or drug- or antigen-encapsulated nanoparticle, microparticle, liposome, or micellar formulation capable of eliciting a biological response in a human or animal. Examples of drug- or antigen-loaded or drug- or antigen-encapsulated formulations include those in which the active agent is encapsulated or loaded into nano- or microparticles, such as biodegradable nano- or microparticles, and which have GIT targeting agents adsorbed, coated or covalently bound, such as directly linked or linked via a linking moiety, onto the surface of the nano- or microparticle. Additionally, the GIT targeting agent can form the nano- or microparticle itself or the GIT targeting agent can be covalently attached to the polymer or polymers used in the production of the biodegradable nano- or microparticles or drug-loaded or drug-encapsulated nano- or microparticles or the peptide can be directly conjugated to the active agent.

The GIT targeting agent bound to the active agent can be employed in methods of treatment (and prophylaxis) by administration to a subject of an effective amount of targeting agent/active agent. Any disease or disorder of interest amenable to therapy or prophylaxis by providing a drug in vivo systemically or by targeting a drug in vivo to the GIT (by linkage to a GIT targeting agent) can be treated or prevented by this administration. Any route of administration known in the art may be used, including but not limited to oral, nasal, topical, intravenous, intraperitoneal, intradermal, mucosal, intrathecal, intramuscular, etc. Preferably, administration is oral.

However, to fully characterize the compositions as well as to determine the fate of the compositions following administration to a subject, antibodies to the specific GIT targeting agents are needed.

SUMMARY OF THE INVENTION

The present invention provides antibodies or antibody fragments specific to a domain of a GIT targeting agent, particularly antibodies to ZElan033 (PAX2 15 mer), ZElan088(HAX42-2 20 mer) and ZElan053 (P31 D-form 16 mer).

Additionally, numerous methods are provided below that employ the GIT targeting agent specific antibodies of this invention, including methods of detecting, quantitating, and locating the GIT targeting agent either in a pharmaceutical composition or after contact of a GIT targeting agent-containing composition with human or animal gastrointestinal tissue.

8, that for Unconj.Ag is SEQ ID NO:1, and that for Zelan103A is SEQ ID NO:9.

Figure 5:
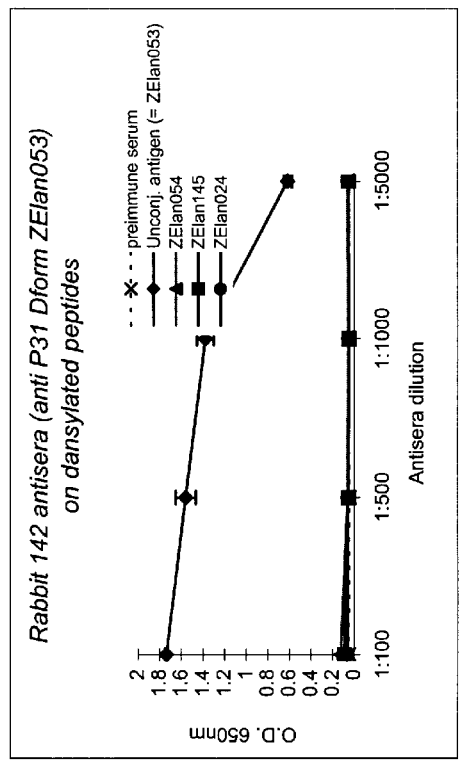
Figure 5:
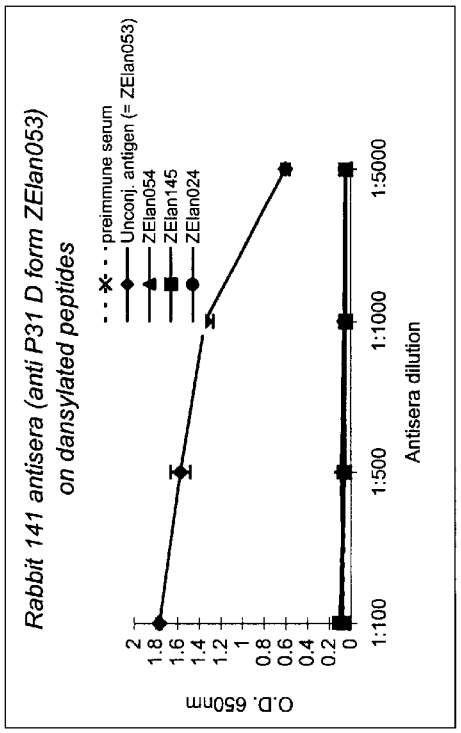
Figure 5:
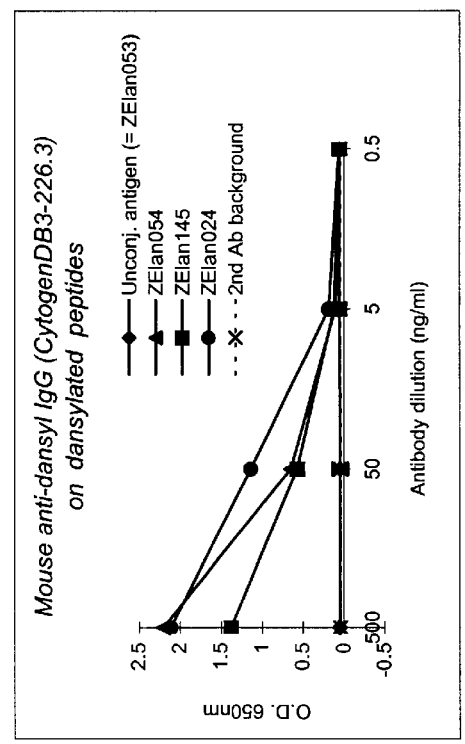

FIG. 5 shows the immuno-reactivity of anti-P31 D-form antisera (fifth bleed samples) on a variety of synthetic peptides. The sequence for Zelan024 is SEQ ID NO:10 in the Sequence Listing herein. The sequence for Unconj.Ag is SEQ ID NO: 3, that for Zelan054 is SEQ ID NO:11, and that for ZElan145 is SEQ ID NO:12.

DETAILED DESCRIPTION OF THE INVENTION

According to this invention, a GIT targeting agent may be used as an immunogen to generate antibodies which immunospecifically bind such an immunogen. Such antibodies include but are not limited to polyclonal, monoclonal, chimeric, single chain, Fab fragments, and a Fab expression library. Particular antibodies provided by this invention include but are not limited to antibodies or antibody fragments, preferably polyclonal antibodies or antibody fragments, specific to a domain of GIT targeting agents ZElan033 (PAX2 15 mer), ZElan088 (HAX42-2 20 mer) and ZElan053 (P31 D-form 16 mer). Additional GIT targeting agents are disclosed throughout the above-referenced WO 98/51325.

The HPT1, hPEPT1, D2H, and hSI receptors were selected for cloning as GIT receptor targets based on several criteria, including: (1) expression on surface of epithelial cells in gastro-intestinal tract (GIT); (2) expression along the length of small intestine (HPT1, hPEPT1, D2H); (3) expression locally at high concentration (hSI); (4) large putative extracellular domains facing into the lumen of the GIT; and (5) extracellular domains that permit easy access and bioadhesion by targeting particles.

The four recombinant receptor sites screened with the peptide libraries additionally have the following characteristics:

| Receptor | Characteristics |
| --- | --- |
| D2H | Transport of neutral/basic amino acids; a transport activating protein for a range of amino acid translocases |
| hS1 | Metabolism of sucrose and other sugars, represents 9% of brush border membrane protein Jejunum |
| HPT1 | di/tri peptide transporter or facilitator of peptide transport |
| hPEPT1 | di/tri peptide transporter |

The following receptor domains were cloned and expressed as His-tag fusion proteins by standard techniques:

Cloning of Extracellular Domain of Selected Receptor Site

| Receptor | Domain (amino acid residues) | SEQ ID NOS |
| --- | --- | --- |
| hPEPT1[a] | 391–571 | 16 |
| HPT1[b] | 29–273 | 15 |
| hSI[c] | 272–667 | 14 |
| D2H[d] | 387–685 | 13 |

[a]Liang et al., 1995, J. Biol. Chem. 270: 6456–6463;
[b]Dantzig et al., 1994, Association of Intestinal Peptide Transport with a Protein Related to the Cadherin Superfamily;
[c]Chantret et al., Biochem. J. 285: 915–923;
[d]Bertran et al., J. Biol. Chem. 268: 14842–14949.

The receptor proteins were expressed as His-tag fusion proteins and affinity purified under denaturing conditions, using urea or guanidine HCl, utilizing the pET His-tag metal chelate affinity for Ni-NTA Agarose (Hochuli, E., Purification of recombinant proteins with metal chelate adsorbent, Genetic Engineering, Principals and Methods (J. K. Setlow, ed.), Plenum Press, NY, Vol. 12 (1990), pp. 87–98).

As indicated in WO 98/51325, phage which showed specificity to a GIT receptor was further characterized by ELISA on a variety of recombinant proteins. Phage which continued to exhibit GIT receptor specificity was sequenced. Their insert sequences are summarized as follows:

| | SEQ. ID. NO | TARGET BINDING PHAGE INSERT SEQUENCE |
| --- | --- | --- |
| hSI | | |
| S15 | 17. | RSGAYESPDGRGGRSYVGGGGGCGNIGRKHNLWGLRTASPACWD |
| S21 | 18. | SPRSFWPWSRHESFGISNYLGCGYRTCISGTMTKSSPIYPRHS |
| S22 | 19. | SSSSDWGGVPGKWRERFKGRGCGISITSVLTGKPNPCPEPKAA |
| Sni10 | 20. | RVGQCTDSDVRRPWARSCAHQGCGAGTRNSHGCITRPLRQASAH |
| Sni28 | 21. | SHSGGMNRAYGDVFRELRDRWNATSHHTRPTPQLPRGPN |
| Sni34 | 22. | SPCGGSWGRFMQGGLFGGRTDGCGAHRNRTSASLEPPSSDY |
| Sni38 | 23. | RGAADQRRGWSENLGLPRVGWDAIAHNSYTFTSRRPRPP |
| Sni45 | 24. | SGGEVSSWGRVNDLCARVSWTGCGTARSARTDNKGFLPKHSSLR |
| SniAX2 | 25. | SDSDGDHYGLRGGVRCSLRDRGCGLALSTVHAGPPSFYPKLSSP |
| SniAX4 | 26. | RSLGNYGVTGTVDVTVLPMPGHANHLGVSSASSSDPPRR |
| SniAX6 | 27. | RTTTAKGCLLGSFGVLSGCSFTPTSPPPHLGYPPHSVN |
| SniAX8 | 28. | SPKLSSVGVMTKVTELPTEGPNAISIPISATLGPRNPLR |
| D2H | | |
| DAB3 | 29. | RWCGAELCNSVTKKFRPGWRDHANPSTHHRTPPPSQSSP |
| DAB7 | 30. | RWCGADDPCGASRWRGGNSLFGCGLRCSMQSTPSGRIHSTSTS |
| DAB10 | 31. | SKSGEGGDSSRGETGWARVRSHAMTAGRFRWYNQLPSDR |
| DAB18 | 32. | RSSANNCEWKSDWMRRACIARYANSSGPARAVDTKAAP |
| DAB24 | 33. | SKWSWSSRWGSPQDKVEKTRAGCGGSPSSTNCHPYTFAPPPQAG |
| DAB30 | 34. | SGFWEFSRGLWDGENRKSVRSGCGFRGSSAQGPCPVTPATIDKH |
| DAX15 | 35. | SESGRCRSVSRWMTTWQTQKGGCGSNVSRGSPLDPSHQTGHATT |
| DAX23 | 36. | REWRFAGPPLDLWAGPSLPSFNASSHPRALRTYWSQRPR |
| DAX24 | 37. | RMEDIKNSGWRDSCRWGDLRPGCGSRQWYPSNMRSSRDYPAGGH |
| DAX27 | 38. | SHPWYRHWNHGDFSGSGQSRHTPPESPHPGRPNATI |
| DCX8 | 39. | RYKHDIGCDAGVDKKSSSVRGGCGAHSSPPRAGRGPRGTMVSRL |
| DCX11 | 40. | SQGSKQCMQYRTGRLTVGSEYGCGMNPARHATPAYPARLLPRYR |
| DCX26 | 41. | SGRTTSEISGLWGWGDDRS GYGWGNTLRPNYIPYRQATNRHRYT |
| DCX33 | 42. | RWNWTVLPATGGHYVVTRSTDYHAINNHRPSIPHQHPTPI |
| DCX36 | 43. | SWSSWNWSSKTTRLGDRATREGCGPSQSDGCPYNGRLTTVKPRT |
| DCX39 | 44. | SGSLNAWQPRSWVGGAFRSHANNNLNPKPTMVTRHPT |
| DCX42 | 45. | RYSGLSPRDNGPACSQEATLEGCGAQRLMSTRRKGRNSRPGWTL |

-continued

| SEQ. ID. NO | | TARGET BINDING PHAGE INSERT SEQUENCE |
|---|---|---|
| DCX45 | 46. | SVGNDKTSRPVSFYGRVSDLWNASLMPK-RTPSSKRHDDG |
| hPEPT1 | | |
| PAX9 | 47. | RWPSVGYKGNGSDTIDVHSNDASTKRS-LIYNHRRPLFP |
| PAX14 | 48. | RTFENDLGVGRSIQKKSDRWYASHN-IRSHFASMSPAGK |
| PAX15 | 49. | SYCRVKGGGEGGHTDSNLARSGCGKVAR-TSRLQHINPRATPPSR |
| PAX16 | 50. | SWTRWGKHTHGGFVNKSPPGKNATSPYTDA QLPSDQGPP |
| PAX17 | 51. | SQVDSFRNSFRWYEPSRALCHGCGKRDTS-TTRIHNSPSDSYPTR |
| PAX18 | 52. | SFLRFQSPRFEDYSRTISRLRN-ATNPSNVSDAHNNRALA |
| PAX35 | 53. | RSITDGGINEVDLSSVSNVLENANS-HRAYRKHRPTLKRP |
| PAX38 | 54. | SSKVSSPRDPTVPRKGGNVDYGCG-HRSSARMPTSALSSITKCYT |
| PAX40 | 55. | RASTQGGRGVAPEFGASVLGRGCGS-ATYYTNSTSCKDAMGHNYS |
| PAX43 | 56. | RWCEKHKFTAARCSAGAGFERDAS-RPPQPAHRDNTNRNA |
| PAX45 | 57. | SFQVYPDHGLERHALDGTGPLYAMP-GRWIRARPQNRDRQ |
| PAX46 | 58. | SRCTDNEQCPDTGTRSRSVSNARYFS-SRLLKTHAPHRP |
| P31 | 59. | SARDSGPAEDGSRAVRLNGVENANTRK-SSRSNPRGRRHP |
| P90 | 60. | SSADAEKCAGSLLWWGRQNNSGCGSP-JKKHLKHRNRSQTSSSSH |
| 5PAX3 | 61. | RPKNVADAYSSQDGAAAEETSHASN-MRKSPKHKPLRRP |
| 5PAX5 | 62. | RGSTGTAGGERSGVLNLHTRDNA SGSGFKPWYPSNRGHK |
| SPAX7 | 63. | RWGWERSPSDYDSDMDLGARRYA-TRTHRAPPRVLKAPLP |
| 5PAX-12 | 64. | RGWKCEGSQMYGDKDIGRSRGCG-SITKNNTNHAHPSHGAVAKI |
| HPT-1 | | |
| HAX9 | 65. | SREEANWDGYKREMSHRSRFWDA-THLSRPRRPANSGDPN |
| HAX35 | 66. | EWYSWKRSSKSTGLGDTATREGC-GPSQSDGCPYNGRLTTVKPRK |
| HAX40 | 67. | REFAERRLWGCDDLSWRLDAEG-CGPTPSNRAVKHRKPRPRSPAL |
| HAX42 | 68. | SDHALGTNLRSDNAKEPGDYNC-CGNGNSTGRKVFNRRRPSAIPT |
| HCA3 | 69. | RHISEYSFANSHLMGGESKRKGCGI-NGSFSPTCPRSPTPAFRRT |
| H40 | 70. | SRESGMWGSWWRGHRLNSTGGNA-NMNASLPPDPPVSTP |
| PAX2 | 71. | STPPSREAYSRPYSVDSDSDTNAKH-SSHNRRLRTRSRPN |

These antibodies can be used in methods relating to the localization and activity of the GIT targeting agent sequences, e.g., for imaging these peptides after in vivo administration (e.g., to monitor treatment efficacy), measuring levels thereof in appropriate physiological samples, in diagnostic methods, etc. For instance, antibodies or antibody fragments specific to a domain of a GIT targeting agent, such as a dansyl group or some other epitope introduced into the peptide, can be used to 1) identify the presence of the peptide on a nanoparticle or other substrate; 2) quantify the amount of peptide on the nanoparticle; 3) measure the level of the peptide in appropriate physiological samples; 4) perform immunohistology on tissue samples; 5) image the peptide after in vivo administration; 6) purify the peptide from a mixture using an immunoaffinity column, 7) bind or fix the peptide to the surface of nanoparticle or 8) when a tag is also added to either an active-agent containing particle or the active agent itself, track the fate of both the particle/active agent and the GIT targeting agent so as to determine if and/or where they become separated. Use 7 above envisions attaching the antibody (or fragment of the antibody) to the surface of drug-loaded nanoparticles or other substrates and then incubating this conjugate with the peptide. This procedure results in binding of the peptide in a certain fixed orientation, resulting in a particle that contains the peptide bound to the antibody in such a way that the peptide is fully active. Additionally, antibodies or antibody fragments specific to a domain of a GIT targeting agent 9) can be used in confocal microscopy imaging techniques or other imaging techniques in order to demonstrate or confirm or identify the location or localization of the peptide on the surface of a nano- or microparticle, 10) can be used in confocal microscopy imaging techniques or other imaging techniques in order to demonstrate or confirm or identify the location or localization of the peptide on the surface of a nanoparticle or microparticle which has also been loaded with a fluorescent agent, 11) in the case of nanoparticles or microparticles coated with the peptide which have been sliced into two halves by a microtone or other suitable techniques, the antibody can be used in suitable quantitative techniques such as confocal microscopy imaging techniques or other quantitative imaging techniques in order to identify or quantitate the relative distribution of the peptide between the surface of the nanoparticle or microparticle and the sub-surface interior matrix of the nanoparticles or microparticles, 12) can be used in confocal microscopy imaging techniques or other imaging techniques in order to demonstrate or confirm or identify the location of a peptide on the surface of a nanoparticle or microparticle which has been loaded with a fluorescent agent such as TRME or fluorascene, 13) can be used to identify which epitope or domain of the peptide is responsible for identification by the antibody; peptide derivatives such as cyclic forms or derivatives containing intra-chain disulphide bonds or other intra-chain bonds can also be used in mapping studies in order to identify which domain or epitope of the peptide is responsible for recognition by the antibody; 14) in the case of peptide derivatives in which the epitope or domain responsible for binding to a target receptor is flanked by di-sulphide bond or other intra-chain bonds and in which this domain is also responsible for binding to the antibody, the antibody can be used to determine if that epitope or domain is exposed or available for binding to the antibody when the peptide or derivative is coated onto the surface of a nanoparticle, microparticle or other substance, 15) can be used where the epitope or domain on the peptide which binds to the target receptors in the human gastro-intestinal tract or the target receptors on model epithelial cells such as Caco-2 cells or polarised Caco-2 cells and where this epitope or domain on the peptide is also responsible for binding by the antibody, the antibody can be used in competition studies to compete for the binding of the peptide to its target receptor sites and 16) where the epitope or domain on the peptide which binds to the target receptors in the human gastro-intestinal or the target receptors on model epithelial cells such as Caco-2 cells or polarised Caco-2 cells and where this epitope or domain on the peptide is also responsible for binding by the antibody, the antibody can be used in competition studies in which nanoparticles or microparticles are coated with the peptide and are used in cell binding studies and/or in receptor binding studies.

Polyclonal antibodies against the GIT targeting agents PAX2 15 mer, HAX42-2 20mer and P31 D-form 16mer were raised to allow for, among other uses as discussed above, following the destiny of particles coated with peptides in in vivo models. These three GIT targeting agents were selected for their ability to bind in vitro to Caco-2 P100 fraction and, when coated on the surface of insulin loaded nanoparticles, to enhance insulin delivery in in vivo studies (rat model/intra-duodenal). The primary sequences for these three GIT targeting agents are given in Table 1.

TABLE 1

| Name | Sequence | | N° of AMINO ACIDS |
|---|---|---|---|
| ZElan033 | K(dns)-TNAKHSSHNRRTRTR (SEQ ID NO: 1) | | PAX2 15 mer |
| ZElan088 | K(dns)-SDNAKEPGDYNCCGNGNSTG (SEQ ID NO: 2) | | HAX-42-2 20 mer |
| ZElan053 | K(dns)-TrKSSrSNPrGrrHPG (SEQ ID NO: 3) | | P31 D form 16 mer |

The peptides were synthesised (Genosys) and conjugated to KLH protein in preparation to immunise rabbits. KLH protein was conjugated at both N- and C-terminals in order to maximise the probability of obtaining specific antibodies.

The immunization protocol provided that two rabbits were immunized for each peptide; Rabbits 122 and 123 were immunized with PAX215 mer, Rabbits 120 and 121 were immunized with HAX42-2 20 mer and Rabbits 141 and 142 were immunized with P31 D-form 16mer. The initial immunisation was given in Complete Freund's adjuvant and the remaining boosts in Incomplete Freunds. A pre-immune sample was taken from each animal before immunization. The rabbits were injected at day 0, day 14 and 28, bled a week later at day 35 (1$^{st}$ bleed), boosted a week later at day 42 and bled a week later at day 49; this sequence of injections and bleeds was performed every two weeks.

The bleed samples were tested by ELISA using the following procedures: 96 well plates were coated with peptide at 50 $\mu$g/ml in 0.05M carbonate/bicarbonate buffer, pH9.6, overnight. The plates were washed twice with PBS+ 0.05% Tween20 and the plates were blocked with 2% dried skimmed milk (99% fat free) in PBS for one hour at room temperature. The plates were then washed three times with PBS+0.05% Tween20 and anti-sera diluted in 2% dried milk-PBS was added followed by incubation for one hour at room temperature. The plates were then washed three times with PBS+0.05% Tween20 and secondary antibody goat anti-rabbit IgG-HRP (Sigma A0545, dilution 1:20000) in 2% dried milk-PBS was added followed by incubation for one hour at room temperature. The plates were washed three times with PBS+0.05% Tween20, TMB substrate was added, incubated and the absorbance was read at 650 nm.

Figure 1:
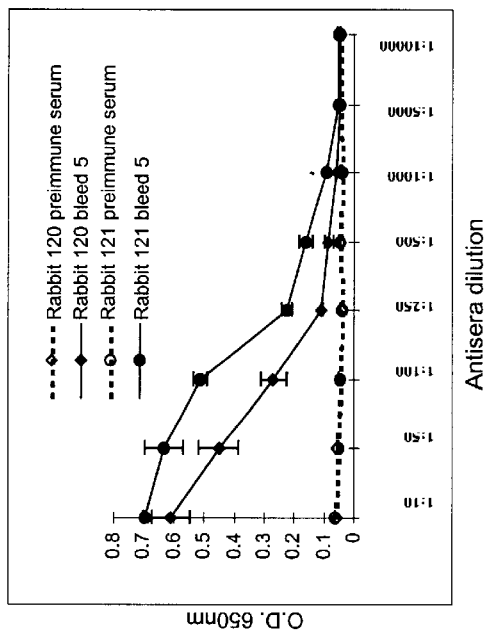
FIG. 1 shows the immuno responses of three groups of 2 rabbits, each group immunized, respectively, with one of KLH conjugated ZElan033, KLH conjugated ZElan088 and KLH conjugated ZElan053, when the fourth bleed samples are tested by ELISA on their respective unconjugated peptides.
Figure 1:
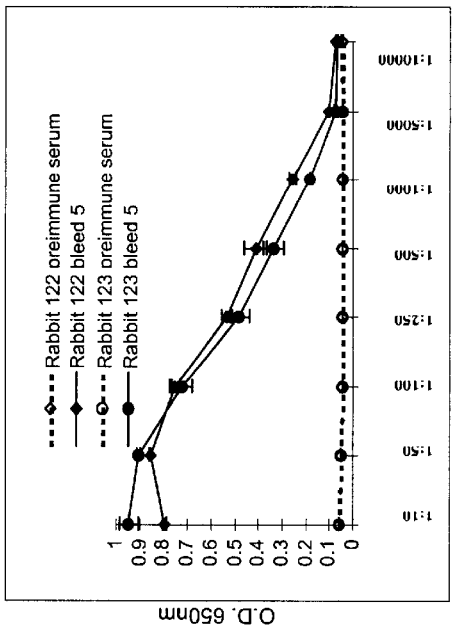
Figure 1:
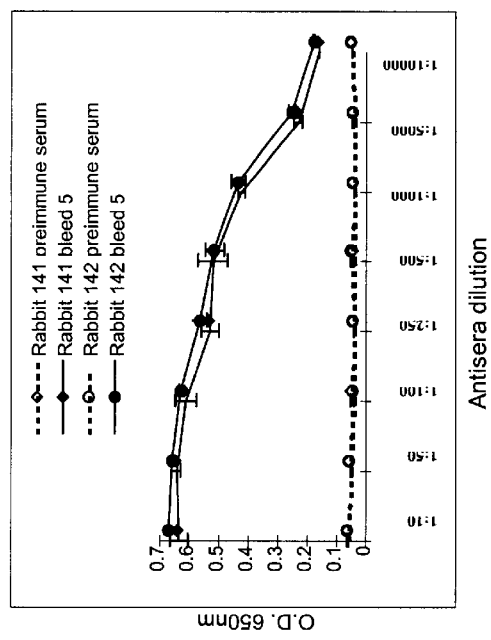
Figure 2:
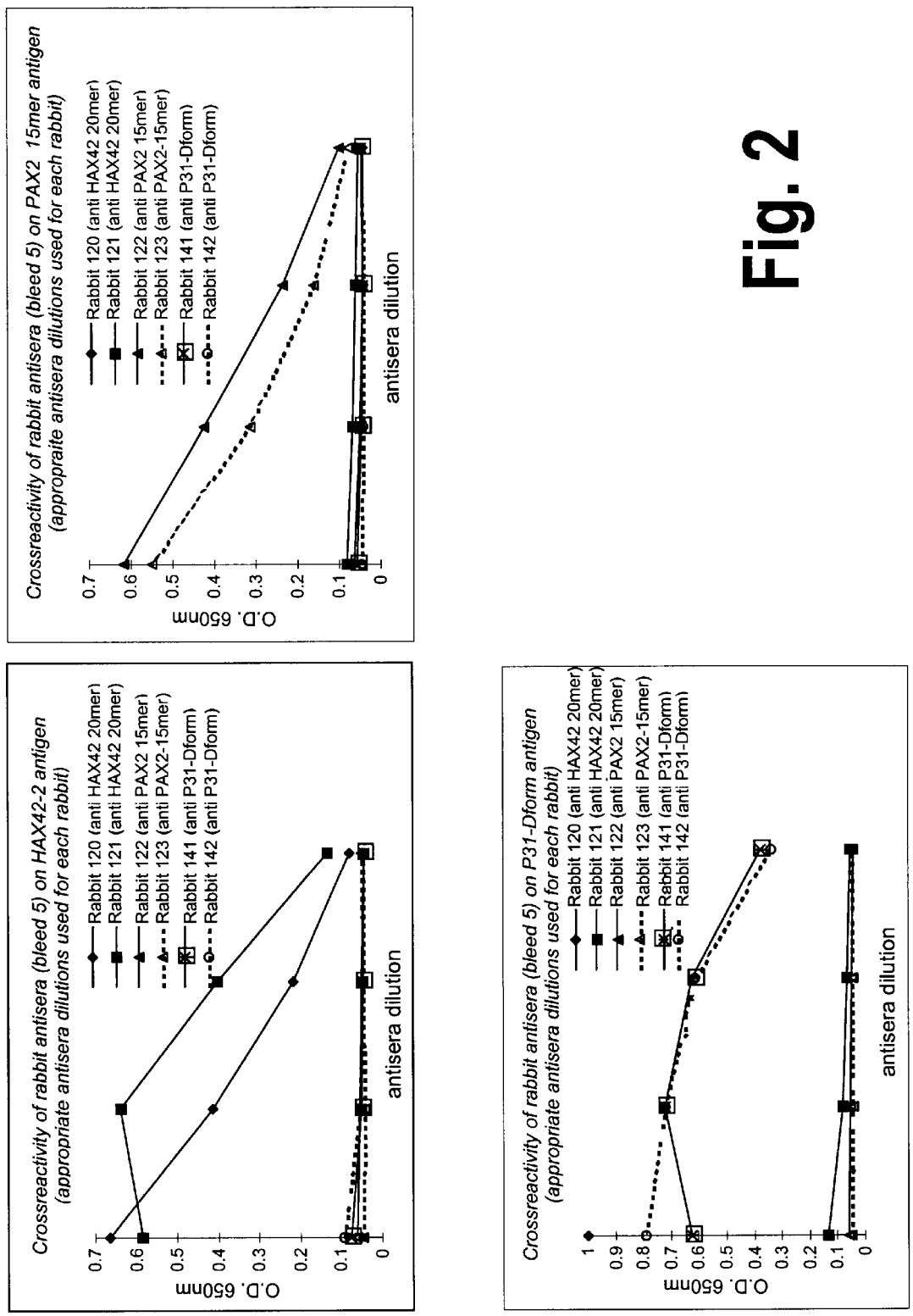
FIG. 2 shows the cross reactivity of rabbit antisera for three groups of 2 rabbits, each group immunized, respectively, with one of KLH conjugated ZElan033, KLH conjugated ZElan088 and KLH conjugated ZElan053, when the fourth bleed samples are tested by ELISA on each of synthetic peptides HAX42.2, PAX 2 15 mer and P31-D-form.

The fourth bleed samples were tested by ELISA on both the peptides used for immunisation (but not conjugated to KLH) and on different (dansylated) peptide batches. Pre-immune serum was included in the assay as negative control and background binding to plastic was also tested. As shown in FIG. 1, the antisera of the immunised rabbits gave an antibody response compared to pre-immune sera of the same animals. The immuno response of the two rabbits immunised in each protocol was comparable except that Rabbit 120 showed a lower antibody titer with respect to Rabbit 121. Crossreactivity of each rabbit antiserum on different peptides was also analysed by ELISA as shown in FIG. 2 and no significant cross-reactivity was detected.

Figure 3:
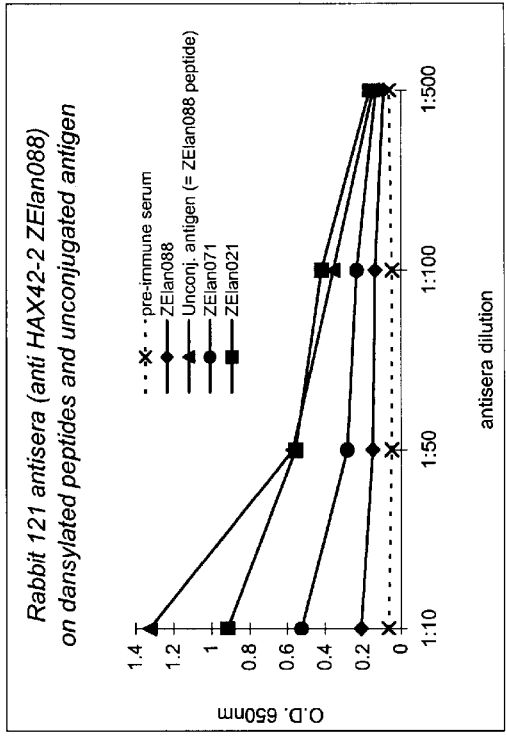
FIG. 3 shows the immuno-reactivity of anti-HAX42-2 antisera (fifth bleed samples) on a variety of synthetic peptides. The sequence for Zelan021 is SEQ ID NO:4 in the Sequence Listing herein. The sequence for Zelan071 is SEQ ID NO: 5, that for Zelan088 is SEQ ID NO:2, and that for Unconj. Antigen is SEQ ID NO:6.
Figure 3:
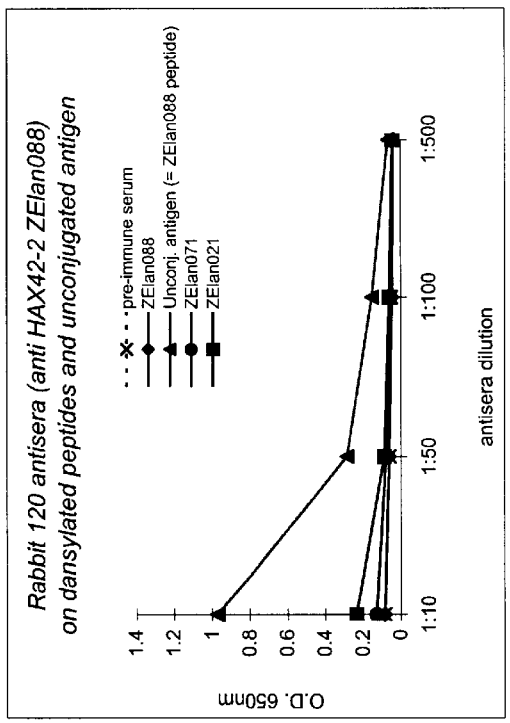
Figure 3:
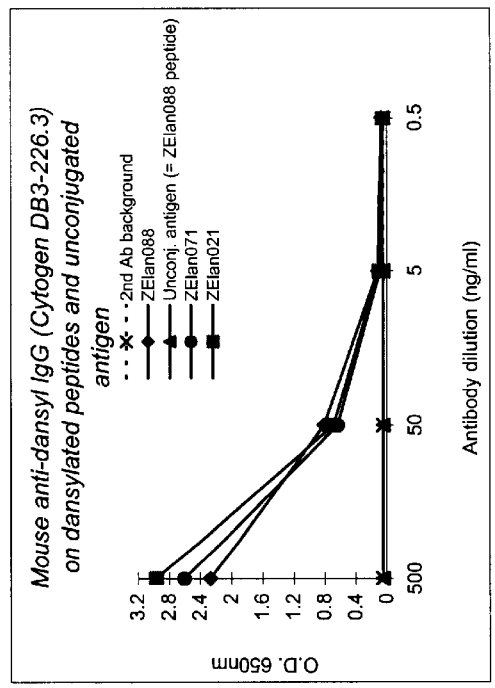
Figure 4:
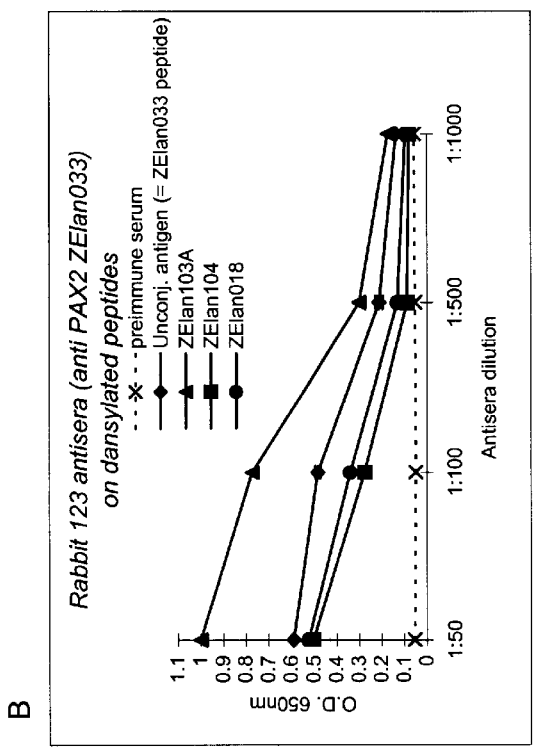
FIG. 4 shows the immuno-reactivity of anti-PAX2 antisera (fifth bleed samples) on a variety of synthetic peptides. The sequence for Zelan108 is SEQ ID NO:7 in the Sequence Listing herein. The sequence for Zelan104 is SEQ ID NO.
Figure 4:
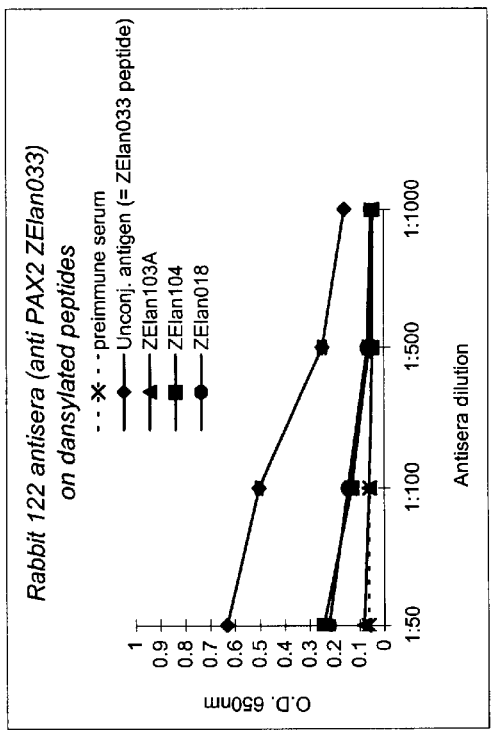
Figure 4:
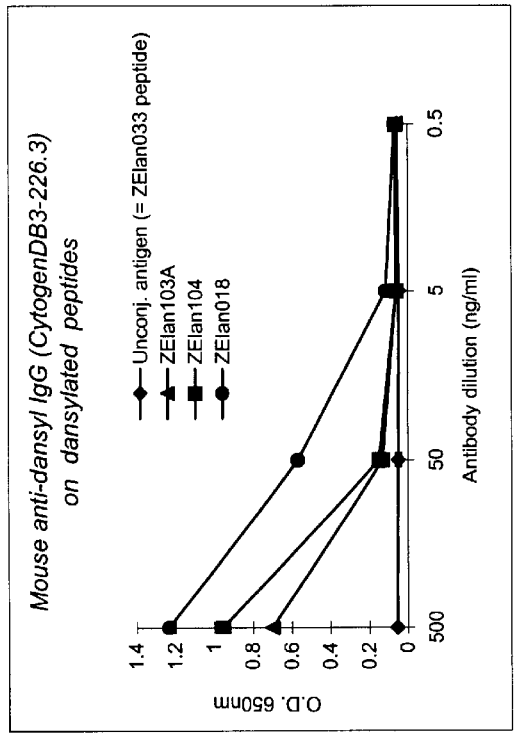

The fifth bleed samples were tested by ELISA as described above and examples of the profiles obtained are shown in FIGS. 3, 4 and 5. A higher titer of antibody was detected for each rabbit after this longer immunisation period compared to the fourth bleed results.

FIG. 3 shows the immuno-reaction of anti-HAX42 antisera on synthetic peptides (sequences reported in the Figure). Panel A shows the ELISA results for rabbit #120 antisera: good immuno-response is obtained on unconjugated peptide used as antigen but no response was obtained for the same peptide conjugated to a dansyl group (Zelan088). No immuno-response is observed for the other peptides analysed. Panel B shows the ELISA results for rabbit #121 antisera: in this case there also was good immuno-response for the unconjugated peptide used as antigen but no response for Zelan088 dansyl-peptide. Rabbit #121 antisera is positive (although less strongly) against Zelan021 (HAX42) and Zelan071 (HAX42 29 mer derivative). Panel C shows the response of anti-dansyl IgG on the peptides used in the assay.

FIG. 4 shows the immuno-reactivity of anti-PAX2 antisera on synthetic peptides. Rabbit #122 (panel A) and #123 (panel B) have a different immuno-response. Both antisera react in the same way to the unconjugated peptide (=Zelan033) used for immunisation. Rabbit #123 antisera has also very strong reactivity against Zelan103A peptide whereas rabbit #122 does not bind to the same peptide. Rabbit #123 antisera has also imuno-response against both Zelan104 and Zelan108. Panel C shows the response of anti-dansyl IgG on the peptides used in the assay.

FIG. 5 shows the immuno-reactivity of anti-P31 D-form antisera on synthetic peptides. Both rabbit #141 and #142 react equally well on P31 D-form unconjugated peptide (=Zelan053). No reactivity is present against all the other peptides tested.

Table 2 provides a summary of the fifth bleed results.

TABLE 2

| | Rabbit Number | Peptides | | | |
|---|---|---|---|---|---|
| | | Zelan021 | Zelan071 | Zelan088 | Unconjug. antigen (= Zelan088) |
| (HAX-42) | Rabbit 120 | − | − | − | + |
| | Rabbit 121 | + | +/− | −/+ | ++ |
| | | Zelan018 | Zelan104 | Unconjug. antigen (= Zelan033) | Zelan103A |
| (PAX2) | Rabbit 122 | −/+ | −/+ | + | − |
| | Rabbit 123 | + | + | + | ++ |
| | | Zelan024 | Unconjug. antigen (= Zelan053) | Zelan054 | Zelan145 |
| (P31 d-form) | Rabbit 141 | − | + | − | − |
| | Rabbit 142 | − | + | − | − |

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. An isolated antibody or antibody fragment specific to a domain of a gastro-intestinal tract (GIT) targeting agent, said targeting agent comprising ZElan033 (PAX2 15 mer) (SEQ ID NO:1).

2. The antibody or antibody fragment of claim 1, wherein the antibody or antibody fragment is selected from the group consisting of a polyclonal antibody, monoclonal antibody, chimeric antibody, single chain antibody, a Fab fragment or a Fab expression library.

* * * * *

SEQUENCE LISTING

<160> NUMBER OF SEQ ID NOS: 84

<210> SEQ ID NO 1
<211> LENGTH: 15
<212> TYPE: PRT
<213> ORGANISM: Artificial Sequence
<220> FEATURE:
<223> OTHER INFORMATION: Random peptide
<220> FEATURE:
<221> NAME/KEY: MISC_FEATURE
<222> LOCATION: (1)..(1)
<223> OTHER INFORMATION: Linked to dansyl group

<400> SEQUENCE: 1

Thr Asn Ala Lys His Ser Ser His Asn Arg Arg Leu Arg Thr Arg
1               5                   10                  15

<210> SEQ ID NO 2
<211> LENGTH: 20
<212> TYPE: PRT
<213> ORGANISM: Artificial Sequence
<220> FEATURE:
<223> OTHER INFORMATION: Random peptide
<220> FEATURE:
<221> NAME/KEY: MISC_FEATURE
<222> LOCATION: (1)..(1)
<223> OTHER INFORMATION: Linked to dansyl group

<400> SEQUENCE: 2

Ser Asp Asn Ala Lys Glu Pro Gly Asp Tyr Asn Cys Cys Gly Asn Gly
1               5                   10                  15

Asn Ser Thr Gly
            20

<210> SEQ ID NO 3
<211> LENGTH: 16
<212> TYPE: PRT
<213> ORGANISM: Artificial Sequence
<220> FEATURE:
<223> OTHER INFORMATION: Random peptide
<220> FEATURE:
<221> NAME/KEY: MISC_FEATURE
<222> LOCATION: (1)..(1)
<223> OTHER INFORMATION: Linked to dansyl group
<220> FEATURE:
<221> NAME/KEY: MISC_FEATURE
<222> LOCATION: (2)..(2)
<223> OTHER INFORMATION: D-amino acid
<220> FEATURE:
<221> NAME/KEY: MISC_FEATURE
<222> LOCATION: (6)..(6)
<223> OTHER INFORMATION: D-amino acid
<220> FEATURE:
<221> NAME/KEY: MISC_FEATURE
<222> LOCATION: (10)..(10)
<223> OTHER INFORMATION: D-amino acid
<220> FEATURE:
<221> NAME/KEY: MISC_FEATURE
<222> LOCATION: (12)..(13)
<223> OTHER INFORMATION: D-amino acid

<400> SEQUENCE: 3

Thr Arg Lys Ser Ser Arg Ser Asn Pro Arg Gly Arg Arg His Pro Gly
1               5                   10                  15

<210> SEQ ID NO 4
<211> LENGTH: 36
<212> TYPE: PRT
<213> ORGANISM: Artificial Sequence

```
<220> FEATURE:
<223> OTHER INFORMATION: Random peptide

<400> SEQUENCE: 4

Ser Asp His Ala Leu Gly Thr Asn Leu Arg Ser Asp Asn Ala Lys Glu
1               5                   10                  15

Pro Gly Asp Tyr Asn Cys Cys Gly Asn Gly Asn Ser Thr Gly Arg Lys
            20                  25                  30

Val Phe Asn Arg
        35

<210> SEQ ID NO 5
<211> LENGTH: 29
<212> TYPE: PRT
<213> ORGANISM: Artificial sequence
<220> FEATURE:
<223> OTHER INFORMATION: Random peptide

<400> SEQUENCE: 5

Asn Leu Arg Ser Asp Asn Ala Lys Glu Pro Gly Asp Tyr Asn Cys Cys
1               5                   10                  15

Gly Asn Gly Asn Ser Thr Gly Arg Lys Val Phe Asn Arg
            20                  25

<210> SEQ ID NO 6
<211> LENGTH: 20
<212> TYPE: PRT
<213> ORGANISM: Artificial Sequence
<220> FEATURE:
<223> OTHER INFORMATION: Random sequence

<400> SEQUENCE: 6

Ser Asp Asn Ala Lys Glu Pro Gly Asp Tyr Asn Cys Cys Gly Asn Gly
1               5                   10                  15

Asn Ser Thr Gly
            20

<210> SEQ ID NO 7
<211> LENGTH: 40
<212> TYPE: PRT
<213> ORGANISM: Artificial Sequence
<220> FEATURE:
<223> OTHER INFORMATION: Random peptide

<400> SEQUENCE: 7

Ser Thr Pro Pro Ser Arg Glu Ala Tyr Ser Arg Pro Tyr Ser Val Asp
1               5                   10                  15

Ser Asp Ser Asp Thr Asn Ala Lys His Ser Ser His Asn Arg Arg Leu
            20                  25                  30

Arg Thr Arg Ser Arg Pro Asn Gly
        35                  40

<210> SEQ ID NO 8
<211> LENGTH: 15
<212> TYPE: PRT
<213> ORGANISM: Artificial Sequence
<220> FEATURE:
<223> OTHER INFORMATION: Cyclic (internal) random peptide

<400> SEQUENCE: 8

Thr Asn Ala Lys His Ser Ser Cys Asn Arg Arg Leu Arg Cys Arg
1               5                   10                  15
```

```
<210> SEQ ID NO 9
<211> LENGTH: 15
<212> TYPE: PRT
<213> ORGANISM: Artificial Sequence
<220> FEATURE:
<223> OTHER INFORMATION: Cyclic (internal) random peptide

<400> SEQUENCE: 9

Thr Asn Ala Lys His Ser Ser Cys Asn Arg Arg Cys Arg Thr Arg
1               5                   10                  15

<210> SEQ ID NO 10
<211> LENGTH: 41
<212> TYPE: PRT
<213> ORGANISM: Artificial Sequence
<220> FEATURE:
<223> OTHER INFORMATION: Random peptide

<400> SEQUENCE: 10

Ser Ala Arg Asp Ser Gly Pro Ala Glu Asp Gly Ser Arg Ala Val Arg
1               5                   10                  15

Leu Asn Gly Val Glu Asn Ala Asn Thr Arg Lys Ser Ser Arg Ser Asn
            20                  25                  30

Pro Arg Gly Arg Arg His Pro Gly Gly
        35                  40

<210> SEQ ID NO 11
<211> LENGTH: 16
<212> TYPE: PRT
<213> ORGANISM: Artificial Sequence
<220> FEATURE:
<223> OTHER INFORMATION: Random peptide
<220> FEATURE:
<221> NAME/KEY: MISC_FEATURE
<222> LOCATION: (6)..(6)
<223> OTHER INFORMATION: D-amino acid
<220> FEATURE:
<221> NAME/KEY: MISC_FEATURE
<222> LOCATION: (12)..(12)
<223> OTHER INFORMATION: D-amino acid

<400> SEQUENCE: 11

Thr Arg Lys Ser Ser Arg Ser Asn Pro Arg Gly Arg Arg His Pro Gly
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Random peptide, D form, retroinversion
<220> FEATURE:
<221> NAME/KEY: MISC_FEATURE
<222> LOCATION: (1)..(16)
<223> OTHER INFORMATION: D-amino acid

<400> SEQUENCE: 12

Gly Pro His Arg Arg Gly Arg Pro Asn Ser Arg Ser Ser Lys Arg Thr
1               5                   10                  15

<210> SEQ ID NO 13
<211> LENGTH: 685
<212> TYPE: PRT
<213> ORGANISM: Artificial
<220> FEATURE:
<223> OTHER INFORMATION: D2H receptor

<400> SEQUENCE: 13
```

-continued

```
Met Ala Glu Asp Lys Ser Lys Arg Asp Ser Ile Glu Met Ser Met Lys
 1               5                  10                  15

Gly Cys Gln Thr Asn Asn Gly Phe Val His Asn Glu Asp Ile Leu Glu
             20                  25                  30

Gln Thr Pro Asp Pro Gly Ser Ser Thr Asp Asn Leu Lys His Ser Thr
         35                  40                  45

Arg Gly Ile Leu Gly Ser Gln Glu Pro Asp Phe Lys Gly Val Gln Pro
 50                  55                  60

Tyr Ala Gly Met Pro Lys Glu Val Leu Phe Gln Phe Ser Gly Gln Ala
65                   70                  75                  80

Arg Tyr Arg Ile Pro Arg Glu Ile Leu Phe Trp Leu Thr Val Ala Ser
                 85                  90                  95

Val Leu Val Leu Ile Ala Ala Thr Ala Ile Ile Ala Leu Ser Pro
             100                 105                 110

Lys Cys Leu Asp Trp Trp Gln Glu Gly Pro Met Tyr Gln Ile Tyr Pro
             115                 120                 125

Arg Ser Phe Lys Asp Ser Asn Lys Asp Gly Asn Gly Asp Leu Lys Gly
         130                 135                 140

Ile Gln Asp Lys Leu Asp Tyr Ile Thr Ala Leu Asn Ile Lys Thr Val
145                 150                 155                 160

Trp Ile Thr Ser Phe Tyr Lys Ser Ser Leu Lys Asp Phe Arg Tyr Gly
                 165                 170                 175

Val Glu Asp Phe Arg Glu Val Asp Pro Ile Phe Gly Thr Met Glu Asp
             180                 185                 190

Phe Glu Asn Leu Val Ala Ala Ile His Asp Lys Gly Leu Lys Leu Ile
         195                 200                 205

Ile Asp Phe Ile Pro Asn His Thr Ser Asp Lys His Ile Trp Phe Gln
210                 215                 220

Leu Ser Arg Thr Arg Thr Gly Lys Tyr Thr Asp Tyr Tyr Ile Trp His
225                 230                 235                 240

Asp Cys Thr His Glu Asn Gly Lys Thr Ile Pro Pro Asn Asn Trp Leu
                 245                 250                 255

Ser Val Tyr Gly Asn Ser Ser Trp His Phe Asp Glu Val Arg Asn Gln
             260                 265                 270

Cys Tyr Phe His Gln Phe Met Lys Glu Gln Pro Asp Leu Asn Phe Arg
         275                 280                 285

Asn Pro Asp Val Gln Glu Ile Lys Glu Ile Leu Arg Phe Trp Leu
290                 295                 300

Thr Lys Gly Val Asp Gly Phe Ser Leu Asp Ala Val Lys Phe Leu Leu
305                 310                 315                 320

Glu Ala Lys His Leu Arg Asp Glu Ile Gln Val Asn Lys Thr Gln Ile
                 325                 330                 335

Pro Asp Thr Val Thr Gln Tyr Ser Glu Leu Tyr His Asp Phe Thr Thr
             340                 345                 350

Thr Gln Val Gly Met His Asp Ile Val Arg Ser Phe Arg Gln Thr Met
         355                 360                 365

Asp Gln Tyr Ser Thr Glu Pro Gly Arg Tyr Arg Phe Met Gly Thr Glu
     370                 375                 380

Ala Tyr Ala Glu Ser Ile Asp Arg Thr Val Met Tyr Tyr Gly Leu Pro
385                 390                 395                 400

Phe Ile Gln Glu Ala Asp Phe Pro Phe Asn Asn Tyr Leu Ser Met Leu
                 405                 410                 415

Asp Thr Val Ser Gly Asn Ser Val Tyr Glu Val Ile Thr Ser Trp Met
```

-continued

```
                420             425             430
Glu Asn Met Pro Glu Gly Lys Trp Pro Asn Trp Met Ile Gly Gly Pro
            435                 440                 445

Asp Ser Ser Arg Leu Thr Ser Arg Leu Gly Asn Gln Tyr Val Asn Val
        450                 455                 460

Met Asn Met Leu Leu Phe Thr Leu Pro Gly Thr Pro Ile Thr Tyr Tyr
465                 470                 475                 480

Gly Glu Glu Ile Gly Met Gly Asn Ile Val Ala Ala Asn Leu Asn Glu
                485                 490                 495

Ser Tyr Asp Ile Asn Thr Leu Arg Ser Lys Ser Pro Met Gln Trp Asp
            500                 505                 510

Asn Ser Ser Asn Ala Gly Phe Ser Glu Ala Ser Asn Thr Trp Leu Pro
        515                 520                 525

Thr Asn Ser Asp Tyr His Thr Val Asn Val Asp Val Gln Lys Thr Gln
    530                 535                 540

Pro Arg Ser Ala Leu Lys Leu Tyr Gln Asp Leu Ser Leu Leu His Ala
545                 550                 555                 560

Asn Glu Leu Leu Leu Asn Arg Gly Trp Phe Cys His Leu Arg Asn Asp
                565                 570                 575

Ser His Tyr Val Val Tyr Thr Arg Glu Leu Asp Gly Ile Asp Arg Ile
            580                 585                 590

Phe Ile Val Val Leu Asn Phe Gly Glu Ser Thr Leu Leu Asn Leu His
        595                 600                 605

Asn Met Ile Ser Gly Leu Pro Ala Lys Ile Arg Ile Arg Leu Ser Thr
    610                 615                 620

Asn Ser Ala Asp Lys Gly Ser Lys Val Asp Thr Ser Gly Ile Phe Leu
625                 630                 635                 640

Asp Lys Gly Glu Gly Leu Ile Phe Glu His Asn Thr Lys Asn Leu Leu
                645                 650                 655

His Arg Gln Thr Ala Phe Arg Asp Arg Cys Phe Val Ser Asn Arg Ala
            660                 665                 670

Cys Tyr Ser Ser Val Leu Asn Ile Leu Tyr Thr Ser Cys
        675                 680                 685
```

<210> SEQ ID NO 14
<211> LENGTH: 1827
<212> TYPE: PRT
<213> ORGANISM: Artificial
<220> FEATURE:
<223> OTHER INFORMATION: hSI receptor

<400> SEQUENCE: 14

```
Met Ala Arg Lys Lys Phe Ser Gly Leu Glu Ile Ser Leu Ile Val Leu
1               5                   10                  15

Phe Val Ile Val Thr Ile Ile Ala Ile Ala Leu Ile Val Val Leu Ala
                20                  25                  30

Thr Lys Thr Pro Ala Val Asp Glu Ile Asp Ser Thr Ser Thr Pro
            35                  40                  45

Ala Thr Thr Arg Val Thr Thr Asn Pro Ser Asp Ser Gly Lys Cys Pro
        50                  55                  60

Asn Val Leu Asn Asp Pro Val Asn Val Arg Ile Asn Cys Ile Pro Glu
65                  70                  75                  80

Gln Phe Pro Thr Glu Gly Ile Cys Ala Gln Arg Gly Cys Cys Trp Arg
                85                  90                  95

Pro Trp Asn Asp Ser Leu Ile Pro Trp Cys Phe Phe Val Asp Asn His
```

```
                    100                 105                 110
Gly Tyr Asn Val Gln Asp Met Thr Thr Thr Ser Ile Gly Val Glu Ala
                115                 120                 125
Lys Leu Asn Arg Ile Pro Ser Pro Thr Leu Phe Gly Asn Asp Ile Asn
130                 135                 140
Ser Val Leu Phe Thr Thr Gln Asn Gln Thr Pro Asn Arg Phe Arg Phe
145                 150                 155                 160
Lys Ile Thr Asp Pro Asn Asn Arg Arg Tyr Glu Val Pro His Gln Tyr
                165                 170                 175
Val Lys Glu Phe Thr Gly Pro Thr Val Ser Asp Thr Leu Tyr Asp Val
                180                 185                 190
Lys Val Ala Gln Asn Pro Phe Ser Ile Gln Val Ile Arg Lys Ser Asn
                195                 200                 205
Gly Lys Thr Leu Phe Asp Thr Ser Ile Gly Pro Leu Val Tyr Ser Asp
                210                 215                 220
Gln Tyr Leu Gln Ile Ser Ala Arg Leu Pro Ser Asp Tyr Ile Tyr Gly
225                 230                 235                 240
Ile Gly Glu Gln Val His Lys Arg Phe Arg His Asp Leu Ser Trp Lys
                245                 250                 255
Thr Trp Pro Ile Phe Thr Arg Asp Gln Leu Pro Gly Asp Asn Asn Asn
                260                 265                 270
Asn Leu Tyr Gly His Gln Thr Phe Phe Met Cys Ile Glu Asp Thr Ser
                275                 280                 285
Gly Lys Ser Phe Gly Val Phe Leu Met Asn Ser Asn Ala Met Glu Ile
                290                 295                 300
Phe Ile Gln Pro Thr Pro Ile Val Thr Tyr Arg Val Thr Gly Gly Ile
305                 310                 315                 320
Leu Asp Phe Tyr Ile Leu Leu Gly Asp Thr Pro Glu Gln Val Val Gln
                325                 330                 335
Gln Tyr Gln Gln Leu Val Gly Leu Pro Ala Met Pro Ala Tyr Trp Asn
                340                 345                 350
Leu Gly Phe Gln Leu Ser Arg Trp Asn Tyr Lys Ser Leu Asp Val Val
                355                 360                 365
Lys Glu Val Val Arg Arg Asn Arg Glu Ala Gly Ile Pro Phe Asp Thr
                370                 375                 380
Gln Val Thr Asp Ile Asp Tyr Met Glu Asp Lys Lys Asp Phe Thr Tyr
385                 390                 395                 400
Asp Gln Val Ala Phe Asn Gly Leu Pro Gln Phe Val Gln Asp Leu His
                405                 410                 415
Asp His Gly Gln Lys Tyr Val Ile Ile Leu Asp Pro Ala Ile Ser Ile
                420                 425                 430
Gly Arg Arg Ala Asn Gly Thr Thr Tyr Ala Thr Tyr Glu Arg Gly Asn
                435                 440                 445
Thr Gln His Val Trp Ile Asn Glu Ser Asp Gly Ser Thr Pro Ile Ile
                450                 455                 460
Gly Glu Val Trp Pro Gly Leu Thr Val Tyr Pro Asp Phe Thr Asn Pro
465                 470                 475                 480
Asn Cys Ile Asp Trp Trp Ala Asn Glu Cys Ser Ile Phe His Gln Glu
                485                 490                 495
Val Gln Tyr Asp Gly Leu Trp Ile Asp Met Asn Glu Val Ser Ser Phe
                500                 505                 510
Ile Gln Gly Ser Thr Lys Gly Cys Asn Val Asn Lys Leu Asn Tyr Pro
                515                 520                 525
```

-continued

```
Pro Phe Thr Pro Asp Ile Leu Asp Lys Leu Met Tyr Ser Lys Thr Ile
    530                 535                 540
Cys Met Asp Ala Val Gln Asn Trp Gly Lys Gln Tyr Asp Val His Ser
545                 550                 555                 560
Leu Tyr Gly Tyr Ser Met Ala Ile Ala Thr Glu Gln Ala Val Gln Lys
            565                 570                 575
Val Phe Pro Asn Lys Arg Ser Phe Ile Leu Thr Arg Ser Thr Phe Ala
            580                 585                 590
Gly Ser Gly Arg His Ala Ala His Trp Leu Gly Asp Asn Thr Ala Ser
            595                 600                 605
Trp Glu Gln Met Glu Trp Ser Ile Thr Gly Met Leu Glu Phe Ser Leu
    610                 615                 620
Phe Gly Ile Pro Leu Val Gly Ala Asp Ile Cys Gly Phe Val Ala Glu
625                 630                 635                 640
Thr Thr Glu Glu Leu Cys Arg Arg Trp Met Gln Leu Gly Ala Phe Tyr
            645                 650                 655
Pro Phe Ser Arg Asn His Asn Ser Asp Gly Tyr Glu His Gln Asp Pro
            660                 665                 670
Ala Phe Phe Gly Gln Asn Ser Leu Leu Val Lys Ser Arg Gln Tyr
            675                 680                 685
Leu Thr Ile Arg Tyr Thr Leu Leu Pro Phe Leu Tyr Thr Leu Phe Tyr
    690                 695                 700
Lys Ala His Val Phe Gly Glu Thr Val Ala Arg Pro Val Leu His Glu
705                 710                 715                 720
Phe Tyr Glu Asp Thr Asn Ser Trp Ile Glu Asp Thr Glu Phe Leu Trp
            725                 730                 735
Gly Pro Ala Leu Leu Ile Thr Pro Val Leu Lys Gln Gly Ala Asp Thr
            740                 745                 750
Val Ser Ala Tyr Ile Pro Asp Ala Ile Trp Tyr Asp Tyr Glu Ser Gly
            755                 760                 765
Ala Lys Arg Pro Trp Arg Lys Gln Arg Val Asp Met Tyr Leu Pro Ala
    770                 775                 780
Asp Lys Ile Gly Leu His Leu Arg Gly Gly Tyr Ile Ile Pro Ile Gln
785                 790                 795                 800
Glu Pro Asp Val Thr Thr Thr Ala Ser Arg Lys Asn Pro Leu Gly Leu
            805                 810                 815
Ile Val Ala Leu Gly Glu Asn Asn Thr Ala Lys Gly Asp Phe Phe Trp
            820                 825                 830
Asp Asp Gly Glu Thr Lys Asp Thr Ile Gln Asn Gly Asn Tyr Ile Leu
            835                 840                 845
Tyr Thr Phe Ser Val Ser Asn Asn Thr Leu Asp Ile Val Cys Thr His
    850                 855                 860
Ser Ser Tyr Gln Glu Gly Thr Thr Leu Ala Phe Gln Thr Val Lys Ile
865                 870                 875                 880
Leu Gly Leu Thr Asp Ser Val Thr Glu Val Arg Val Ala Glu Asn Asn
            885                 890                 895
Gln Pro Met Asn Ala His Ser Asn Phe Thr Tyr Asp Ala Ser Asn Gln
            900                 905                 910
Val Leu Leu Ile Ala Asp Leu Lys Leu Asn Leu Gly Arg Asn Phe Ser
            915                 920                 925
Val Gln Trp Asn Gln Ile Phe Ser Glu Asn Glu Arg Phe Asn Cys Tyr
    930                 935                 940
```

-continued

```
Pro Asp Ala Asp Leu Ala Thr Glu Gln Lys Cys Thr Gln Arg Gly Cys
945                 950                 955                 960

Val Trp Arg Thr Gly Ser Ser Leu Ser Lys Ala Pro Glu Cys Tyr Phe
                965                 970                 975

Pro Arg Gln Asp Asn Ser Tyr Ser Val Asn Ser Ala Arg Tyr Ser Ser
            980                 985                 990

Met Gly Ile Thr Ala Asp Leu Gln Leu Asn Thr Ala Asn Ala Arg Ile
        995                 1000                1005

Lys Leu Pro Ser Asp Pro Ile Ser Thr Leu Arg Val Glu Val Lys
    1010                1015                1020

Tyr His Lys Asn Asp Met Leu Gln Phe Lys Ile Tyr Asp Pro Gln
    1025                1030                1035

Lys Lys Arg Tyr Glu Val Pro Val Pro Leu Asn Ile Pro Thr Thr
    1040                1045                1050

Pro Ile Ser Thr Tyr Glu Asp Arg Leu Tyr Asp Val Glu Ile Lys
    1055                1060                1065

Glu Asn Pro Phe Gly Ile Gln Ile Arg Arg Arg Ser Ser Gly Arg
    1070                1075                1080

Val Ile Trp Asp Ser Trp Leu Pro Gly Phe Ala Phe Asn Asp Gln
    1085                1090                1095

Phe Ile Gln Ile Ser Thr Arg Leu Pro Ser Glu Tyr Ile Tyr Gly
    1100                1105                1110

Phe Gly Glu Val Glu His Thr Ala Phe Lys Arg Asp Leu Asn Trp
    1115                1120                1125

Asn Thr Trp Gly Met Phe Thr Arg Asp Gln Pro Pro Gly Tyr Lys
    1130                1135                1140

Leu Asn Ser Tyr Gly Phe His Pro Tyr Tyr Met Ala Leu Glu Glu
    1145                1150                1155

Glu Gly Asn Ala His Gly Val Phe Leu Leu Asn Ser Asn Ala Met
    1160                1165                1170

Asp Val Thr Phe Gln Pro Thr Pro Ala Leu Thr Tyr Arg Thr Val
    1175                1180                1185

Gly Gly Ile Leu Asp Phe Tyr Met Phe Leu Gly Pro Thr Pro Gln
    1190                1195                1200

Val Ala Thr Lys Gln Tyr His Glu Val Ile Gly His Pro Val Met
    1205                1210                1215

Pro Ala Tyr Trp Ala Leu Gly Phe Gln Leu Cys Arg Tyr Gly Tyr
    1220                1225                1230

Ala Asn Thr Ser Glu Val Arg Glu Leu Tyr Asp Ala Met Val Ala
    1235                1240                1245

Ala Asn Ile Pro Tyr Asp Val Gln Tyr Thr Asp Ile Asp Tyr Met
    1250                1255                1260

Glu Arg Gln Leu Asp Phe Thr Ile Gly Glu Ala Phe Gln Asp Leu
    1265                1270                1275

Pro Gln Phe Val Asp Lys Ile Arg Gly Glu Gly Met Arg Tyr Ile
    1280                1285                1290

Ile Ile Leu Asp Pro Ala Ile Ser Gly Asn Glu Thr Lys Thr Tyr
    1295                1300                1305

Pro Ala Phe Glu Arg Gly Gln Gln Asn Asp Val Phe Val Lys Trp
    1310                1315                1320

Pro Asn Thr Asn Asp Ile Cys Trp Ala Lys Val Trp Pro Asp Leu
    1325                1330                1335

Pro Asn Ile Thr Ile Asp Lys Thr Leu Thr Glu Asp Glu Ala Val
```

-continued

```
                1340                1345                1350
Asn Ala Ser Arg Ala His Val Ala Phe Pro Asp Phe Phe Arg Thr
    1355                1360                1365
Ser Thr Ala Glu Trp Trp Ala Arg Glu Ile Val Asp Phe Tyr Asn
    1370                1375                1380
Glu Lys Met Lys Phe Asp Gly Leu Trp Ile Asp Met Asn Glu Pro
    1385                1390                1395
Ser Ser Phe Val Asn Gly Thr Thr Thr Asn Gln Cys Arg Asn Asp
    1400                1405                1410
Glu Leu Asn Tyr Pro Pro Tyr Phe Pro Glu Leu Thr Lys Arg Thr
    1415                1420                1425
Asp Gly Leu His Phe Arg Thr Ile Cys Met Glu Ala Glu Gln Ile
    1430                1435                1440
Leu Ser Asp Gly Thr Ser Val Leu His Tyr Asp Val His Asn Leu
    1445                1450                1455
Tyr Gly Trp Ser Gln Met Lys Pro Thr His Asp Ala Leu Gln Lys
    1460                1465                1470
Thr Thr Gly Lys Arg Gly Ile Val Ile Ser Arg Ser Thr Tyr Pro
    1475                1480                1485
Thr Ser Gly Arg Trp Gly Gly His Trp Leu Gly Asp Asn Tyr Ala
    1490                1495                1500
Arg Trp Asp Asn Met Asp Lys Ser Ile Ile Gly Met Met Glu Phe
    1505                1510                1515
Ser Leu Phe Gly Ile Ser Tyr Thr Gly Ala Asp Ile Cys Gly Phe
    1520                1525                1530
Phe Asn Asn Ser Glu Tyr His Leu Cys Thr Arg Trp Met Gln Leu
    1535                1540                1545
Gly Ala Phe Tyr Pro Tyr Ser Arg Asn His Asn Ile Ala Asn Thr
    1550                1555                1560
Arg Arg Gln Asp Pro Ala Ser Trp Asn Glu Thr Phe Ala Glu Met
    1565                1570                1575
Ser Arg Asn Ile Leu Asn Ile Arg Tyr Thr Leu Leu Pro Tyr Phe
    1580                1585                1590
Tyr Thr Gln Met His Glu Ile His Ala Asn Gly Gly Thr Val Ile
    1595                1600                1605
Arg Pro Leu Leu His Glu Phe Phe Asp Glu Lys Pro Thr Trp Asp
    1610                1615                1620
Ile Phe Lys Gln Phe Leu Trp Gly Pro Ala Phe Met Val Thr Pro
    1625                1630                1635
Val Leu Glu Pro Tyr Val Gln Thr Val Asn Ala Tyr Val Pro Asn
    1640                1645                1650
Ala Arg Trp Phe Asp Tyr His Thr Gly Lys Asp Ile Gly Val Arg
    1655                1660                1665
Gly Gln Phe Gln Thr Phe Asn Ala Ser Tyr Asp Thr Ile Asn Leu
    1670                1675                1680
His Val Arg Gly Gly His Ile Leu Pro Cys Gln Glu Pro Ala Gln
    1685                1690                1695
Asn Thr Phe Tyr Ser Arg Gln Lys His Met Lys Leu Ile Val Ala
    1700                1705                1710
Ala Asp Asp Asn Gln Met Ala Gln Gly Ser Leu Phe Trp Asp Asp
    1715                1720                1725
Gly Glu Ser Ile Asp Thr Tyr Glu Arg Asp Leu Tyr Leu Ser Val
    1730                1735                1740
```

-continued

```
Gln Phe Asn Leu Asn Gln Thr Thr Leu Thr Ser Thr Ile Leu Lys
    1745                1750                1755

Arg Gly Tyr Ile Asn Lys Ser Glu Thr Arg Leu Gly Ser Leu His
    1760                1765                1770

Val Trp Gly Lys Gly Thr Thr Pro Val Asn Ala Val Thr Leu Thr
    1775                1780                1785

Tyr Asn Gly Asn Lys Asn Ser Leu Pro Phe Asn Glu Asp Thr Thr
    1790                1795                1800

Asn Met Ile Leu Arg Ile Asp Leu Thr His Asn Val Thr Leu
    1805                1810                1815

Glu Glu Pro Ile Glu Ile Asn Trp Ser
    1820                1825
```

<210> SEQ ID NO 15
<211> LENGTH: 832
<212> TYPE: PRT
<213> ORGANISM: Artificial
<220> FEATURE:
<223> OTHER INFORMATION: HPT1 receptor

<400> SEQUENCE: 15

```
Met Ile Leu Gln Ala His Leu His Ser Leu Cys Leu Leu Met Leu Tyr
1               5                   10                  15

Leu Ala Thr Gly Tyr Gly Gln Glu Gly Lys Phe Ser Gly Pro Leu Lys
            20                  25                  30

Pro Met Thr Phe Ser Ile Tyr Glu Gly Gln Glu Pro Ser Gln Ile Ile
        35                  40                  45

Phe Gln Phe Lys Ala Asn Pro Pro Ala Val Thr Phe Glu Leu Thr Gly
    50                  55                  60

Glu Thr Asp Asn Ile Phe Val Ile Glu Arg Glu Gly Leu Leu Tyr Tyr
65                  70                  75                  80

Asn Arg Ala Leu Asp Arg Glu Thr Arg Ser Thr His Asn Leu Gln Val
                85                  90                  95

Ala Ala Leu Asp Ala Asn Gly Ile Ile Val Glu Gly Pro Val Pro Ile
            100                 105                 110

Thr Ile Glu Val Lys Asp Ile Asn Asp Asn Arg Pro Thr Phe Leu Gln
        115                 120                 125

Ser Lys Tyr Glu Gly Ser Val Arg Gln Asn Ser Arg Pro Gly Lys Pro
    130                 135                 140

Phe Leu Tyr Val Asn Ala Thr Asp Leu Asp Asp Pro Ala Thr Pro Asn
145                 150                 155                 160

Gly Gln Leu Tyr Tyr Gln Ile Val Ile Gln Leu Pro Met Ile Asn Asn
                165                 170                 175

Val Met Tyr Phe Gln Ile Asn Asn Lys Thr Gly Ala Ile Ser Leu Thr
            180                 185                 190

Arg Glu Gly Ser Gln Glu Leu Asn Pro Ala Lys Asn Pro Ser Tyr Asn
        195                 200                 205

Leu Val Ile Ser Val Lys Asp Met Gly Gly Gln Ser Glu Asn Ser Phe
    210                 215                 220

Ser Asp Thr Thr Ser Val Asp Ile Ile Val Thr Glu Asn Ile Trp Lys
225                 230                 235                 240

Ala Pro Lys Pro Val Glu Met Val Glu Asn Ser Thr Asp Pro His Pro
                245                 250                 255

Ile Lys Ile Thr Gln Val Arg Trp Asn Asp Pro Gly Ala Gln Tyr Ser
            260                 265                 270
```

-continued

```
Leu Val Asp Lys Glu Lys Leu Pro Arg Phe Pro Phe Ser Ile Asp Gln
            275                 280                 285
Glu Gly Asp Ile Tyr Val Thr Gln Pro Leu Asp Arg Glu Glu Lys Asp
        290                 295                 300
Ala Tyr Val Phe Tyr Ala Val Ala Lys Asp Glu Tyr Gly Lys Pro Leu
305                 310                 315                 320
Ser Tyr Pro Leu Glu Ile His Val Lys Val Lys Asp Ile Asn Asp Asn
                325                 330                 335
Pro Pro Thr Cys Pro Ser Pro Val Thr Val Phe Glu Val Gln Glu Asn
            340                 345                 350
Glu Arg Leu Gly Asn Ser Ile Gly Thr Leu Thr Ala His Asp Arg Asp
        355                 360                 365
Glu Glu Asn Thr Ala Asn Ser Phe Leu Asn Tyr Arg Ile Val Glu Gln
370                 375                 380
Thr Pro Lys Leu Pro Met Asp Gly Leu Phe Leu Ile Gln Thr Tyr Ala
385                 390                 395                 400
Gly Met Leu Gln Leu Ala Lys Gln Ser Leu Lys Lys Gln Asp Thr Pro
                405                 410                 415
Gln Tyr Asn Leu Thr Ile Glu Val Ser Asp Lys Asp Phe Lys Thr Leu
            420                 425                 430
Cys Phe Val Gln Ile Asn Val Ile Asp Ile Asn Asp Gln Ile Pro Ile
        435                 440                 445
Phe Glu Lys Ser Asp Tyr Gly Asn Leu Thr Leu Ala Glu Asp Thr Asn
    450                 455                 460
Ile Gly Ser Thr Ile Leu Thr Ile Gln Ala Thr Asp Ala Asp Glu Pro
465                 470                 475                 480
Phe Thr Gly Ser Ser Lys Ile Leu Tyr His Ile Ile Lys Gly Asp Ser
                485                 490                 495
Glu Gly Arg Leu Gly Val Asp Thr Asp Pro His Thr Asn Thr Gly Tyr
            500                 505                 510
Val Ile Ile Lys Lys Pro Leu Asp Phe Glu Thr Ala Ala Val Ser Asn
        515                 520                 525
Ile Val Phe Lys Ala Glu Asn Pro Glu Pro Leu Val Phe Gly Val Lys
    530                 535                 540
Tyr Asn Ala Ser Ser Phe Ala Lys Phe Thr Leu Ile Val Thr Asp Val
545                 550                 555                 560
Asn Glu Ala Pro Gln Phe Ser Gln His Val Phe Gln Ala Lys Val Ser
                565                 570                 575
Glu Asp Val Ala Ile Gly Thr Lys Val Gly Asn Val Thr Ala Lys Asp
            580                 585                 590
Pro Glu Gly Leu Asp Ile Ser Tyr Ser Leu Arg Gly Asp Thr Arg Gly
        595                 600                 605
Trp Leu Lys Ile Asp His Val Thr Gly Glu Ile Phe Ser Val Ala Pro
    610                 615                 620
Leu Asp Arg Glu Ala Gly Ser Pro Tyr Arg Val Gln Val Val Ala Thr
625                 630                 635                 640
Glu Val Gly Gly Ser Ser Leu Ser Ser Val Ser Glu Phe His Leu Ile
                645                 650                 655
Leu Met Asp Val Asn Asp Asn Pro Pro Arg Leu Ala Lys Asp Tyr Thr
            660                 665                 670
Gly Leu Phe Phe Cys His Pro Leu Ser Ala Pro Gly Ser Leu Ile Phe
        675                 680                 685
```

```
Glu Ala Thr Asp Asp Gln His Leu Phe Arg Gly Pro His Phe Thr
    690             695                 700

Phe Ser Leu Gly Ser Gly Ser Leu Gln Asn Asp Trp Glu Val Ser Lys
705             710                 715                 720

Ile Asn Gly Thr His Ala Arg Leu Ser Thr Arg His Thr Asp Phe Glu
                725                 730                 735

Glu Arg Ala Tyr Val Val Leu Ile Arg Ile Asn Asp Gly Gly Arg Pro
            740                 745                 750

Pro Leu Glu Gly Ile Val Ser Leu Pro Val Thr Phe Cys Ser Cys Val
        755                 760                 765

Glu Gly Ser Cys Phe Arg Pro Ala Gly His Gln Thr Gly Ile Pro Thr
    770                 775                 780

Val Gly Met Ala Val Gly Ile Leu Leu Thr Thr Leu Leu Val Ile Gly
785             790                 795                 800

Ile Ile Leu Ala Val Val Phe Ile Arg Ile Lys Lys Asp Lys Gly Lys
                805                 810                 815

Asp Asn Val Glu Ser Ala Gln Ala Ser Glu Val Lys Pro Leu Arg Ser
            820                 825                 830
```

<210> SEQ ID NO 16
<211> LENGTH: 708
<212> TYPE: PRT
<213> ORGANISM: Artificial
<220> FEATURE:
<223> OTHER INFORMATION: hPEPT1 receptor

<400> SEQUENCE: 16

```
Met Gly Met Ser Lys Ser His Ser Phe Phe Gly Tyr Pro Leu Ser Ile
1               5                   10                  15

Phe Phe Ile Val Val Asn Glu Phe Cys Glu Arg Phe Ser Tyr Tyr Gly
                20                  25                  30

Met Arg Ala Ile Leu Ile Leu Tyr Phe Thr Asn Phe Ile Ser Trp Asp
            35                  40                  45

Asp Asn Leu Ser Thr Ala Ile Tyr His Thr Phe Val Ala Leu Cys Tyr
        50                  55                  60

Leu Thr Pro Ile Leu Gly Ala Leu Ile Ala Asp Ser Trp Leu Gly Lys
65                  70                  75                  80

Phe Lys Thr Ile Val Ser Leu Ser Ile Val Tyr Thr Ile Gly Gln Ala
                85                  90                  95

Val Thr Ser Val Ser Ser Ile Asn Asp Leu Thr Asp His Asn His Asp
            100                 105                 110

Gly Thr Pro Asp Ser Leu Pro Val His Val Val Leu Ser Leu Ile Gly
        115                 120                 125

Leu Ala Leu Ile Ala Leu Gly Thr Gly Gly Ile Lys Pro Cys Val Ser
130                 135                 140

Ala Phe Gly Gly Asp Gln Phe Glu Glu Gly Gln Lys Gln Arg Asn
145                 150                 155             160

Arg Phe Phe Ser Ile Phe Tyr Leu Ala Ile Asn Ala Gly Ser Leu Leu
                165                 170                 175

Ser Thr Ile Ile Thr Pro Met Leu Arg Val Gln Gln Cys Gly Ile His
            180                 185                 190

Ser Lys Gln Ala Cys Tyr Pro Leu Ala Phe Gly Val Pro Ala Ala Leu
        195                 200                 205

Met Ala Val Ala Leu Ile Val Phe Val Leu Gly Ser Gly Met Tyr Lys
210                 215                 220
```

-continued

```
Lys Phe Lys Pro Gln Gly Asn Ile Met Gly Lys Val Ala Lys Cys Ile
225                 230                 235                 240

Gly Phe Ala Ile Lys Asn Arg Phe Arg His Arg Ser Lys Ala Phe Pro
            245                 250                 255

Lys Arg Glu His Trp Leu Asp Trp Ala Lys Glu Lys Tyr Asp Glu Arg
                260                 265                 270

Leu Ile Ser Gln Ile Lys Met Val Thr Arg Val Met Phe Leu Tyr Ile
            275                 280                 285

Pro Leu Pro Met Phe Trp Ala Leu Phe Asp Gln Gln Gly Ser Arg Trp
    290                 295                 300

Thr Leu Gln Ala Thr Thr Met Ser Gly Lys Ile Gly Ala Leu Glu Ile
305                 310                 315                 320

Gln Pro Asp Gln Met Gln Thr Val Asn Ala Ile Leu Ile Val Ile Met
                325                 330                 335

Val Pro Ile Phe Asp Ala Val Leu Tyr Pro Leu Ile Ala Lys Cys Gly
            340                 345                 350

Phe Asn Phe Thr Ser Leu Lys Lys Met Ala Val Gly Met Val Leu Ala
            355                 360                 365

Ser Met Ala Phe Val Val Ala Ala Ile Val Gln Val Glu Ile Asp Lys
    370                 375                 380

Thr Leu Pro Val Phe Pro Lys Gly Asn Glu Val Gln Ile Lys Val Leu
385                 390                 395                 400

Asn Ile Gly Asn Asn Thr Met Asn Ile Ser Leu Pro Gly Glu Met Val
                405                 410                 415

Thr Leu Gly Pro Met Ser Gln Thr Asn Ala Phe Met Thr Phe Asp Val
            420                 425                 430

Asn Lys Leu Thr Arg Ile Asn Ile Ser Ser Pro Gly Ser Pro Val Thr
            435                 440                 445

Ala Val Thr Asp Asp Phe Lys Gln Gly Gln Arg His Thr Leu Leu Val
    450                 455                 460

Trp Ala Pro Asn His Tyr Gln Val Val Lys Asp Gly Leu Asn Gln Lys
465                 470                 475                 480

Pro Glu Lys Gly Glu Asn Gly Ile Arg Phe Val Asn Thr Phe Asn Glu
                485                 490                 495

Leu Ile Thr Ile Thr Met Ser Gly Lys Val Tyr Ala Asn Ile Ser Ser
            500                 505                 510

Tyr Asn Ala Ser Thr Tyr Gln Phe Phe Pro Ser Gly Ile Lys Gly Phe
            515                 520                 525

Thr Ile Ser Ser Thr Glu Ile Pro Pro Gln Cys Gln Pro Asn Phe Asn
    530                 535                 540

Thr Phe Tyr Leu Glu Phe Gly Ser Ala Tyr Thr Tyr Ile Val Gln Arg
545                 550                 555                 560

Lys Asn Asp Ser Cys Pro Glu Val Lys Val Phe Glu Asp Ile Ser Ala
                565                 570                 575

Asn Thr Val Asn Met Ala Leu Gln Ile Pro Gln Tyr Phe Leu Leu Thr
            580                 585                 590

Cys Gly Glu Val Val Phe Ser Val Thr Gly Leu Glu Phe Ser Tyr Ser
            595                 600                 605

Gln Ala Pro Ser Asn Met Lys Ser Val Leu Gln Ala Gly Trp Leu Leu
    610                 615                 620

Thr Val Ala Val Gly Asn Ile Ile Val Leu Ile Val Ala Gly Ala Gly
625                 630                 635                 640

Gln Phe Ser Lys Gln Trp Ala Glu Tyr Ile Leu Phe Ala Ala Leu Leu
```

-continued

```
                        645                 650                 655
Leu Val Val Cys Val Val Phe Ala Ile Met Ala Arg Phe Tyr Thr Tyr
                660                 665                 670
Ile Asn Pro Ala Glu Ile Glu Ala Gln Phe Asp Glu Asp Glu Lys Lys
            675                 680                 685
Asn Arg Leu Glu Lys Ser Asn Pro Tyr Phe Met Ser Gly Ala Asn Ser
        690                 695                 700
Gln Lys Gln Met
705

<210> SEQ ID NO 17
<211> LENGTH: 44
<212> TYPE: PRT
<213> ORGANISM: Artificial
<220> FEATURE:
<223> OTHER INFORMATION: S15 44 mer fragment L-form

<400> SEQUENCE: 17

Arg Ser Gly Ala Tyr Glu Ser Pro Asp Gly Arg Gly Gly Arg Ser Tyr
1               5                   10                  15
Val Gly Gly Gly Gly Cys Gly Asn Ile Gly Arg Lys His Asn Leu
            20                  25                  30
Trp Gly Leu Arg Thr Ala Ser Pro Ala Cys Trp Asp
        35                  40

<210> SEQ ID NO 18
<211> LENGTH: 44
<212> TYPE: PRT
<213> ORGANISM: Artificial
<220> FEATURE:
<223> OTHER INFORMATION: S21 44 mer fragment L-form

<400> SEQUENCE: 18

Ser Pro Arg Ser Phe Trp Pro Val Val Ser Arg His Glu Ser Phe Gly
1               5                   10                  15
Ile Ser Asn Tyr Leu Gly Cys Gly Tyr Arg Thr Cys Ile Ser Gly Thr
            20                  25                  30
Met Thr Lys Ser Ser Pro Ile Tyr Pro Arg His Ser
        35                  40

<210> SEQ ID NO 19
<211> LENGTH: 44
<212> TYPE: PRT
<213> ORGANISM: Artificial
<220> FEATURE:
<223> OTHER INFORMATION: S22 44 mer fragment L-form

<400> SEQUENCE: 19

Ser Ser Ser Ser Asp Trp Gly Gly Val Pro Gly Lys Val Val Arg Glu
1               5                   10                  15
Arg Phe Lys Gly Arg Gly Cys Gly Ile Ser Ile Thr Ser Val Leu Thr
            20                  25                  30
Gly Lys Pro Asn Pro Cys Pro Glu Pro Lys Ala Ala
        35                  40

<210> SEQ ID NO 20
<211> LENGTH: 44
<212> TYPE: PRT
<213> ORGANISM: Artificial
<220> FEATURE:
<223> OTHER INFORMATION: Sni10 44 mer fragment L-form
```

```
<400> SEQUENCE: 20

Arg Val Gly Gln Cys Thr Asp Ser Asp Val Arg Arg Pro Trp Ala Arg
1               5                   10                  15

Ser Cys Ala His Gln Gly Cys Gly Ala Gly Thr Arg Asn Ser His Gly
                20                  25                  30

Cys Ile Thr Arg Pro Leu Arg Gln Ala Ser Ala His
            35                  40

<210> SEQ ID NO 21
<211> LENGTH: 39
<212> TYPE: PRT
<213> ORGANISM: Artificial
<220> FEATURE:
<223> OTHER INFORMATION: Sni28 39 mer fragment L-form

<400> SEQUENCE: 21

Ser His Ser Gly Gly Met Asn Arg Ala Tyr Gly Asp Val Phe Arg Glu
1               5                   10                  15

Leu Arg Asp Arg Trp Asn Ala Thr Ser His His Thr Arg Pro Thr Pro
                20                  25                  30

Gln Leu Pro Arg Gly Pro Asn
            35

<210> SEQ ID NO 22
<211> LENGTH: 41
<212> TYPE: PRT
<213> ORGANISM: Artificial
<220> FEATURE:
<223> OTHER INFORMATION: Sni34 41 mer fragment L-form

<400> SEQUENCE: 22

Ser Pro Cys Gly Gly Ser Trp Gly Arg Phe Met Gln Gly Gly Leu Phe
1               5                   10                  15

Gly Gly Arg Thr Asp Gly Cys Gly Ala His Arg Asn Arg Thr Ser Ala
                20                  25                  30

Ser Leu Glu Pro Pro Ser Ser Asp Tyr
            35                  40

<210> SEQ ID NO 23
<211> LENGTH: 39
<212> TYPE: PRT
<213> ORGANISM: Artificial
<220> FEATURE:
<223> OTHER INFORMATION: Sni38 39 mer fragment L-form

<400> SEQUENCE: 23

Arg Gly Ala Ala Asp Gln Arg Arg Gly Trp Ser Glu Asn Leu Gly Leu
1               5                   10                  15

Pro Arg Val Gly Trp Asp Ala Ile Ala His Asn Ser Tyr Thr Phe Thr
                20                  25                  30

Ser Arg Arg Pro Arg Pro Pro
            35

<210> SEQ ID NO 24
<211> LENGTH: 44
<212> TYPE: PRT
<213> ORGANISM: Artificial
<220> FEATURE:
<223> OTHER INFORMATION: Sni45 44 mer fragment L-form

<400> SEQUENCE: 24

Ser Gly Gly Glu Val Ser Ser Trp Gly Arg Val Asn Asp Leu Cys Ala
```

```
            1               5              10              15
Arg Val Ser Trp Thr Gly Cys Gly Thr Ala Arg Ser Ala Arg Thr Asp
                    20              25              30

Asn Lys Gly Phe Leu Pro Lys His Ser Ser Leu Arg
            35              40
```

<210> SEQ ID NO 25
<211> LENGTH: 44
<212> TYPE: PRT
<213> ORGANISM: Artificial
<220> FEATURE:
<223> OTHER INFORMATION: SniAX2 44 mer fragment L-form

<400> SEQUENCE: 25

```
Ser Asp Ser Asp Gly Asp His Tyr Gly Leu Arg Gly Gly Val Arg Cys
 1               5              10              15

Ser Leu Arg Asp Arg Gly Cys Gly Leu Ala Leu Ser Thr Val His Ala
                    20              25              30

Gly Pro Pro Ser Phe Tyr Pro Lys Leu Ser Ser Pro
            35              40
```

<210> SEQ ID NO 26
<211> LENGTH: 39
<212> TYPE: PRT
<213> ORGANISM: Artificial
<220> FEATURE:
<223> OTHER INFORMATION: SniAX4 39 mer fragment L-form

<400> SEQUENCE: 26

```
Arg Ser Leu Gly Asn Tyr Gly Val Thr Gly Thr Val Asp Val Thr Val
 1               5              10              15

Leu Pro Met Pro Gly His Ala Asn His Leu Gly Val Ser Ser Ala Ser
                    20              25              30

Ser Ser Asp Pro Pro Arg Arg
            35
```

<210> SEQ ID NO 27
<211> LENGTH: 38
<212> TYPE: PRT
<213> ORGANISM: Artificial
<220> FEATURE:
<223> OTHER INFORMATION: SniAX6 38 mer fragment L-form

<400> SEQUENCE: 27

```
Arg Thr Thr Thr Ala Lys Gly Cys Leu Leu Gly Ser Phe Gly Val Leu
 1               5              10              15

Ser Gly Cys Ser Phe Thr Pro Thr Ser Pro Pro His Leu Gly Tyr
                    20              25              30

Pro Pro His Ser Val Asn
            35
```

<210> SEQ ID NO 28
<211> LENGTH: 39
<212> TYPE: PRT
<213> ORGANISM: Artificial
<220> FEATURE:
<223> OTHER INFORMATION: SniAX8 39 mer fragment L-form

<400> SEQUENCE: 28

```
Ser Pro Lys Leu Ser Ser Val Gly Val Met Thr Lys Val Thr Glu Leu
 1               5              10              15

Pro Thr Glu Gly Pro Asn Ala Ile Ser Ile Pro Ile Ser Ala Thr Leu
```

20                  25                  30

Gly Pro Arg Asn Pro Leu Arg
         35

<210> SEQ ID NO 29
<211> LENGTH: 39
<212> TYPE: PRT
<213> ORGANISM: Artificial
<220> FEATURE:
<223> OTHER INFORMATION: DAB3 39 mer fragment L-form

<400> SEQUENCE: 29

Arg Trp Cys Gly Ala Glu Leu Cys Asn Ser Val Thr Lys Lys Phe Arg
1               5                   10                  15

Pro Gly Trp Arg Asp His Ala Asn Pro Ser Thr His His Arg Thr Pro
            20                  25                  30

Pro Pro Ser Gln Ser Ser Pro
         35

<210> SEQ ID NO 30
<211> LENGTH: 44
<212> TYPE: PRT
<213> ORGANISM: Artificial
<220> FEATURE:
<223> OTHER INFORMATION: DAB7 44 mer fragment L-form

<400> SEQUENCE: 30

Arg Trp Cys Gly Ala Asp Asp Pro Cys Gly Ala Ser Arg Trp Arg Gly
1               5                   10                  15

Gly Asn Ser Leu Phe Gly Cys Gly Leu Arg Cys Ser Ala Ala Gln Ser
            20                  25                  30

Thr Pro Ser Gly Arg Ile His Ser Thr Ser Thr Ser
         35                  40

<210> SEQ ID NO 31
<211> LENGTH: 39
<212> TYPE: PRT
<213> ORGANISM: Artificial
<220> FEATURE:
<223> OTHER INFORMATION: DAB10 39 mer fragment L-form

<400> SEQUENCE: 31

Ser Lys Ser Gly Glu Gly Gly Asp Ser Arg Gly Glu Thr Gly Trp
1               5                   10                  15

Ala Arg Val Arg Ser His Ala Met Thr Ala Gly Arg Phe Arg Trp Tyr
            20                  25                  30

Asn Gln Leu Pro Ser Asp Arg
         35

<210> SEQ ID NO 32
<211> LENGTH: 38
<212> TYPE: PRT
<213> ORGANISM: Artificial
<220> FEATURE:
<223> OTHER INFORMATION: DAB18 38 mer fragment L-form

<400> SEQUENCE: 32

Arg Ser Ser Ala Asn Asn Cys Glu Trp Lys Ser Asp Trp Met Arg Arg
1               5                   10                  15

Ala Cys Ile Ala Arg Tyr Ala Asn Ser Ser Gly Pro Ala Arg Ala Val
            20                  25                  30

Asp Thr Lys Ala Ala Pro

<210> SEQ ID NO 33
<211> LENGTH: 44
<212> TYPE: PRT
<213> ORGANISM: Artificial
<220> FEATURE:
<223> OTHER INFORMATION: DAB24 44 mer fragment L-form

<400> SEQUENCE: 33

Ser Lys Trp Ser Trp Ser Ser Arg Trp Gly Ser Pro Gln Asp Lys Val
1               5                   10                  15

Glu Lys Thr Arg Ala Gly Cys Gly Ser Pro Ser Ser Thr Asn Cys
            20                  25                  30

His Pro Tyr Thr Phe Ala Pro Pro Gln Ala Gly
        35                  40

<210> SEQ ID NO 34
<211> LENGTH: 44
<212> TYPE: PRT
<213> ORGANISM: Artificial
<220> FEATURE:
<223> OTHER INFORMATION: DAB30 44 mer fragment L-form

<400> SEQUENCE: 34

Ser Gly Phe Trp Glu Phe Ser Arg Gly Leu Trp Asp Gly Glu Asn Arg
1               5                   10                  15

Lys Ser Val Arg Ser Gly Cys Gly Phe Arg Gly Ser Ser Ala Gln Gly
            20                  25                  30

Pro Cys Pro Val Thr Pro Ala Thr Ile Asp Lys His
        35                  40

<210> SEQ ID NO 35
<211> LENGTH: 44
<212> TYPE: PRT
<213> ORGANISM: Artificial
<220> FEATURE:
<223> OTHER INFORMATION: DAX15 44 mer fragment L-form

<400> SEQUENCE: 35

Ser Glu Ser Gly Arg Cys Arg Ser Val Ser Arg Trp Met Thr Thr Trp
1               5                   10                  15

Gln Thr Gln Lys Gly Gly Cys Gly Ser Asn Val Ser Arg Gly Ser Pro
            20                  25                  30

Leu Asp Pro Ser His Gln Thr Gly His Ala Thr Thr
        35                  40

<210> SEQ ID NO 36
<211> LENGTH: 39
<212> TYPE: PRT
<213> ORGANISM: Artificial
<220> FEATURE:
<223> OTHER INFORMATION: DAX23 39 mer fragment L-form

<400> SEQUENCE: 36

Arg Glu Trp Arg Phe Ala Gly Pro Pro Leu Asp Leu Trp Ala Gly Pro
1               5                   10                  15

Ser Leu Pro Ser Phe Asn Ala Ser Ser His Pro Arg Ala Leu Arg Thr
            20                  25                  30

Tyr Trp Ser Gln Arg Pro Arg
        35

```
<210> SEQ ID NO 37
<211> LENGTH: 44
<212> TYPE: PRT
<213> ORGANISM: Artificial
<220> FEATURE:
<223> OTHER INFORMATION: DAX24 44 mer fragment L-form

<400> SEQUENCE: 37

Arg Met Glu Asp Ile Lys Asn Ser Gly Trp Arg Asp Ser Cys Arg Trp
1               5                   10                  15

Gly Asp Leu Arg Pro Gly Cys Gly Ser Arg Gln Trp Tyr Pro Ser Asn
            20                  25                  30

Met Arg Ser Ser Arg Asp Tyr Pro Ala Gly Gly His
        35                  40

<210> SEQ ID NO 38
<211> LENGTH: 36
<212> TYPE: PRT
<213> ORGANISM: Artificial
<220> FEATURE:
<223> OTHER INFORMATION: DAX27 36 mer fragment L-form

<400> SEQUENCE: 38

Ser His Pro Trp Tyr Arg His Trp Asn His Gly Asp Phe Ser Gly Ser
1               5                   10                  15

Gly Gln Ser Arg His Thr Pro Pro Glu Ser Pro His Pro Gly Arg Pro
            20                  25                  30

Asn Ala Thr Ile
        35

<210> SEQ ID NO 39
<211> LENGTH: 44
<212> TYPE: PRT
<213> ORGANISM: Artificial
<220> FEATURE:
<223> OTHER INFORMATION: DCX8 44 mer fragment L-form

<400> SEQUENCE: 39

Arg Tyr Lys His Asp Ile Gly Cys Asp Ala Gly Val Asp Lys Lys Ser
1               5                   10                  15

Ser Ser Val Arg Gly Gly Cys Gly Ala His Ser Ser Pro Pro Arg Ala
            20                  25                  30

Gly Arg Gly Pro Arg Gly Thr Met Val Ser Arg Leu
        35                  40

<210> SEQ ID NO 40
<211> LENGTH: 44
<212> TYPE: PRT
<213> ORGANISM: Artificial
<220> FEATURE:
<223> OTHER INFORMATION: DCX11 44 mer fragment L-form

<400> SEQUENCE: 40

Ser Gln Gly Ser Lys Gln Cys Met Gln Tyr Arg Thr Gly Arg Leu Thr
1               5                   10                  15

Val Gly Ser Glu Tyr Gly Cys Gly Met Asn Pro Ala Arg His Ala Thr
            20                  25                  30

Pro Ala Tyr Pro Ala Arg Leu Leu Pro Arg Tyr Arg
        35                  40

<210> SEQ ID NO 41
<211> LENGTH: 44
<212> TYPE: PRT
```

```
<213> ORGANISM: Artificial
<220> FEATURE:
<223> OTHER INFORMATION: DCX26 44 mer fragment L-form

<400> SEQUENCE: 41

Ser Gly Arg Thr Thr Ser Glu Ile Ser Gly Leu Trp Gly Trp Gly Asp
1               5                   10                  15

Asp Arg Ser Gly Tyr Gly Trp Gly Asn Thr Leu Arg Pro Asn Tyr Ile
            20                  25                  30

Pro Tyr Arg Gln Ala Thr Asn Arg His Arg Tyr Thr
        35                  40

<210> SEQ ID NO 42
<211> LENGTH: 39
<212> TYPE: PRT
<213> ORGANISM: Artificial
<220> FEATURE:
<223> OTHER INFORMATION: DCX33 39 mer fragment L-form

<400> SEQUENCE: 42

Arg Trp Asn Trp Thr Val Leu Pro Ala Thr Gly Gly His Tyr Trp Thr
1               5                   10                  15

Arg Ser Thr Asp Tyr His Ala Ile Asn Asn His Arg Pro Ser Ile Pro
            20                  25                  30

His Gln His Pro Thr Pro Ile
        35

<210> SEQ ID NO 43
<211> LENGTH: 44
<212> TYPE: PRT
<213> ORGANISM: Artificial
<220> FEATURE:
<223> OTHER INFORMATION: DCX36 44 mer fragment L-form

<400> SEQUENCE: 43

Ser Trp Ser Ser Trp Asn Trp Ser Ser Lys Thr Thr Arg Leu Gly Asp
1               5                   10                  15

Arg Ala Thr Arg Glu Gly Cys Gly Pro Ser Gln Ser Asp Gly Cys Pro
            20                  25                  30

Tyr Asn Gly Arg Leu Thr Thr Val Lys Pro Arg Thr
        35                  40

<210> SEQ ID NO 44
<211> LENGTH: 37
<212> TYPE: PRT
<213> ORGANISM: Artificial
<220> FEATURE:
<223> OTHER INFORMATION: DCX39 37 mer fragment L-form

<400> SEQUENCE: 44

Ser Gly Ser Leu Asn Ala Trp Gln Pro Arg Ser Trp Val Gly Gly Ala
1               5                   10                  15

Phe Arg Ser His Ala Asn Asn Asn Leu Asn Pro Lys Pro Thr Met Val
            20                  25                  30

Thr Arg His Pro Thr
        35

<210> SEQ ID NO 45
<211> LENGTH: 44
<212> TYPE: PRT
<213> ORGANISM: Artificial
<220> FEATURE:
<223> OTHER INFORMATION: DCX42 44 mer fragment L-form
```

<400> SEQUENCE: 45

Arg Tyr Ser Gly Leu Ser Pro Arg Asp Asn Gly Pro Ala Cys Ser Gln
1               5                   10                  15

Glu Ala Thr Leu Glu Gly Cys Gly Ala Gln Arg Leu Met Ser Thr Arg
            20                  25                  30

Arg Lys Gly Arg Asn Ser Arg Pro Gly Trp Thr Leu
        35                  40

<210> SEQ ID NO 46
<211> LENGTH: 39
<212> TYPE: PRT
<213> ORGANISM: Artificial
<220> FEATURE:
<223> OTHER INFORMATION: DCX45 39 mer fragment L-form

<400> SEQUENCE: 46

Ser Val Gly Asn Asp Lys Thr Ser Arg Pro Val Ser Phe Tyr Gly Arg
1               5                   10                  15

Val Ser Asp Leu Trp Asn Ala Ser Leu Met Pro Lys Arg Thr Pro Ser
            20                  25                  30

Ser Lys Arg His Asp Asp Gly
        35

<210> SEQ ID NO 47
<211> LENGTH: 38
<212> TYPE: PRT
<213> ORGANISM: Artificial
<220> FEATURE:
<223> OTHER INFORMATION: PAX9 38 mer fragment L-form

<400> SEQUENCE: 47

Arg Trp Pro Ser Val Gly Tyr Lys Gly Asn Gly Ser Asp Thr Ile Asp
1               5                   10                  15

Val His Ser Asn Asp Ala Ser Thr Lys Arg Ser Leu Ile Tyr Asn His
            20                  25                  30

Arg Arg Pro Leu Phe Pro
        35

<210> SEQ ID NO 48
<211> LENGTH: 39
<212> TYPE: PRT
<213> ORGANISM: Artificial
<220> FEATURE:
<223> OTHER INFORMATION: PAX14 39 mer fragment L-form

<400> SEQUENCE: 48

Arg Thr Phe Glu Asn Asp Gly Leu Gly Val Gly Arg Ser Ile Gln Lys
1               5                   10                  15

Lys Ser Asp Arg Trp Tyr Ala Ser His Asn Ile Arg Ser His Phe Ala
            20                  25                  30

Ser Met Ser Pro Ala Gly Lys
        35

<210> SEQ ID NO 49
<211> LENGTH: 44
<212> TYPE: PRT
<213> ORGANISM: Artificial
<220> FEATURE:
<223> OTHER INFORMATION: PAX15 44 mer fragment L-form

<400> SEQUENCE: 49

-continued

```
Ser Tyr Cys Arg Val Lys Gly Gly Gly Glu Gly Gly His Thr Asp Ser
1               5                   10                  15

Asn Leu Ala Arg Ser Gly Cys Gly Lys Val Ala Arg Thr Ser Arg Leu
            20                  25                  30

Gln His Ile Asn Pro Arg Ala Thr Pro Pro Ser Arg
        35                  40

<210> SEQ ID NO 50
<211> LENGTH: 39
<212> TYPE: PRT
<213> ORGANISM: Artificial
<220> FEATURE:
<223> OTHER INFORMATION: PAX16 39 mer fragment L-form

<400> SEQUENCE: 50

Ser Trp Thr Arg Trp Gly Lys His Thr His Gly Gly Phe Val Asn Lys
1               5                   10                  15

Ser Pro Pro Gly Lys Asn Ala Thr Ser Pro Tyr Thr Asp Ala Gln Leu
            20                  25                  30

Pro Ser Asp Gln Gly Pro Pro
        35

<210> SEQ ID NO 51
<211> LENGTH: 44
<212> TYPE: PRT
<213> ORGANISM: Artificial
<220> FEATURE:
<223> OTHER INFORMATION: PAX17 44 mer fragment L-form

<400> SEQUENCE: 51

Ser Gln Val Asp Ser Phe Arg Asn Ser Phe Arg Trp Tyr Glu Pro Ser
1               5                   10                  15

Arg Ala Leu Cys His Gly Cys Gly Lys Arg Asp Thr Ser Thr Thr Arg
            20                  25                  30

Ile His Asn Ser Pro Ser Asp Ser Tyr Pro Thr Arg
        35                  40

<210> SEQ ID NO 52
<211> LENGTH: 39
<212> TYPE: PRT
<213> ORGANISM: Artificial
<220> FEATURE:
<223> OTHER INFORMATION: PAX18 39 mer fragment L-form

<400> SEQUENCE: 52

Ser Phe Leu Arg Phe Gln Ser Pro Arg Phe Glu Asp Tyr Ser Arg Thr
1               5                   10                  15

Ile Ser Arg Leu Arg Asn Ala Thr Asn Pro Ser Asn Val Ser Asp Ala
            20                  25                  30

His Asn Asn Arg Ala Leu Ala
        35

<210> SEQ ID NO 53
<211> LENGTH: 39
<212> TYPE: PRT
<213> ORGANISM: Artificial
<220> FEATURE:
<223> OTHER INFORMATION: PAX35 39 mer fragment L-form

<400> SEQUENCE: 53

Arg Ser Ile Thr Asp Gly Gly Leu Asn Glu Val Asp Leu Ser Ser Val
1               5                   10                  15
```

-continued

```
Ser Asn Val Leu Glu Asn Ala Asn Ser His Arg Ala Tyr Arg Lys His
            20                  25                  30

Arg Pro Thr Leu Lys Arg Pro
        35
```

<210> SEQ ID NO 54
<211> LENGTH: 44
<212> TYPE: PRT
<213> ORGANISM: Artificial
<220> FEATURE:
<223> OTHER INFORMATION: PAX38 44 mer fragment L-form

<400> SEQUENCE: 54

```
Ser Ser Lys Val Ser Ser Pro Arg Asp Pro Thr Val Pro Arg Lys Gly
1               5                   10                  15

Gly Asn Val Asp Tyr Gly Cys Gly His Arg Ser Ser Ala Arg Met Pro
            20                  25                  30

Thr Ser Ala Leu Ser Ser Ile Thr Lys Cys Tyr Thr
        35                  40
```

<210> SEQ ID NO 55
<211> LENGTH: 44
<212> TYPE: PRT
<213> ORGANISM: Artificial
<220> FEATURE:
<223> OTHER INFORMATION: PAX40 44 mer fragment L-form

<400> SEQUENCE: 55

```
Arg Ala Ser Thr Gln Gly Gly Arg Gly Val Ala Pro Glu Phe Gly Ala
1               5                   10                  15

Ser Val Leu Gly Arg Gly Cys Gly Ser Ala Thr Tyr Tyr Thr Asn Ser
            20                  25                  30

Thr Ser Cys Lys Asp Ala Met Gly His Asn Tyr Ser
        35                  40
```

<210> SEQ ID NO 56
<211> LENGTH: 39
<212> TYPE: PRT
<213> ORGANISM: Artificial
<220> FEATURE:
<223> OTHER INFORMATION: PAX43 39 mer fragment L-form

<400> SEQUENCE: 56

```
Arg Trp Cys Glu Lys His Lys Phe Thr Ala Ala Arg Cys Ser Ala Gly
1               5                   10                  15

Ala Gly Phe Glu Arg Asp Ala Ser Arg Pro Pro Gln Pro Ala His Arg
            20                  25                  30

Asp Asn Thr Asn Arg Asn Ala
        35
```

<210> SEQ ID NO 57
<211> LENGTH: 39
<212> TYPE: PRT
<213> ORGANISM: Artificial
<220> FEATURE:
<223> OTHER INFORMATION: PAX45 39 mer fragment L-form

<400> SEQUENCE: 57

```
Ser Phe Gln Val Tyr Pro Asp His Gly Leu Glu Arg His Ala Leu Asp
1               5                   10                  15

Gly Thr Gly Pro Leu Tyr Ala Met Pro Gly Arg Trp Leu Arg Ala Arg
            20                  25                  30
```

```
Pro Gln Asn Arg Asp Arg Gln
        35

<210> SEQ ID NO 58
<211> LENGTH: 38
<212> TYPE: PRT
<213> ORGANISM: Artificial
<220> FEATURE:
<223> OTHER INFORMATION: PAX46 38 mer fragment L-form

<400> SEQUENCE: 58

Ser Arg Cys Thr Asp Asn Glu Gln Cys Pro Asp Thr Gly Thr Arg Ser
1               5                  10                  15

Arg Ser Val Ser Asn Ala Arg Tyr Phe Ser Ser Arg Leu Leu Lys Thr
            20                  25                  30

His Ala Pro His Arg Pro
        35

<210> SEQ ID NO 59
<211> LENGTH: 39
<212> TYPE: PRT
<213> ORGANISM: Artificial
<220> FEATURE:
<223> OTHER INFORMATION: P31 39 mer fragment L-form

<400> SEQUENCE: 59

Ser Ala Arg Asp Ser Gly Pro Ala Glu Asp Gly Ser Arg Ala Val Arg
1               5                  10                  15

Leu Asn Gly Val Glu Asn Ala Asn Thr Arg Lys Ser Ser Arg Ser Asn
            20                  25                  30

Pro Arg Gly Arg Arg His Pro
        35

<210> SEQ ID NO 60
<211> LENGTH: 44
<212> TYPE: PRT
<213> ORGANISM: Artificial
<220> FEATURE:
<223> OTHER INFORMATION: P90 44 mer fragment L-form

<400> SEQUENCE: 60

Ser Ser Ala Asp Ala Glu Lys Cys Ala Gly Ser Leu Leu Trp Trp Gly
1               5                  10                  15

Arg Gln Asn Asn Ser Gly Cys Gly Ser Pro Thr Lys Lys His Leu Lys
            20                  25                  30

His Arg Asn Arg Ser Gln Thr Ser Ser Ser His
        35                  40

<210> SEQ ID NO 61
<211> LENGTH: 39
<212> TYPE: PRT
<213> ORGANISM: Artificial
<220> FEATURE:
<223> OTHER INFORMATION: 5PAX3 39 mer fragment L-form

<400> SEQUENCE: 61

Arg Pro Lys Asn Val Ala Asp Ala Tyr Ser Ser Gln Asp Gly Ala Ala
1               5                  10                  15

Ala Glu Glu Thr Ser His Ala Ser Asn Ala Ala Arg Lys Ser Pro Lys
            20                  25                  30

His Lys Pro Leu Arg Arg Pro
        35
```

```
<210> SEQ ID NO 62
<211> LENGTH: 39
<212> TYPE: PRT
<213> ORGANISM: Artificial
<220> FEATURE:
<223> OTHER INFORMATION: 5PAX5 39 mer fragment L-form

<400> SEQUENCE: 62
```

Arg Gly Ser Thr Gly Thr Ala Gly Gly Glu Arg Ser Gly Val Leu Asn
1               5                   10                  15

Leu His Thr Arg Asp Asn Ala Ser Gly Ser Gly Phe Lys Pro Trp Tyr
            20                  25                  30

Pro Ser Asn Arg Gly His Lys
        35

```
<210> SEQ ID NO 63
<211> LENGTH: 39
<212> TYPE: PRT
<213> ORGANISM: Artificial
<220> FEATURE:
<223> OTHER INFORMATION: 5PAX7 39 mer fragment L-form

<400> SEQUENCE: 63
```

Arg Trp Gly Trp Glu Arg Ser Pro Ser Asp Tyr Asp Ser Asp Met Asp
1               5                   10                  15

Leu Gly Ala Arg Arg Tyr Ala Thr Arg Thr His Arg Ala Pro Pro Arg
            20                  25                  30

Val Leu Lys Ala Pro Leu Pro
        35

```
<210> SEQ ID NO 64
<211> LENGTH: 44
<212> TYPE: PRT
<213> ORGANISM: Artificial
<220> FEATURE:
<223> OTHER INFORMATION: 5PAX12 44 mer fragment L-form

<400> SEQUENCE: 64
```

Arg Gly Trp Lys Cys Glu Gly Ser Gln Ala Ala Tyr Gly Asp Lys Asp
1               5                   10                  15

Ile Gly Arg Ser Arg Gly Cys Gly Ser Ile Thr Lys Asn Asn Thr Asn
            20                  25                  30

His Ala His Pro Ser His Gly Ala Val Ala Lys Ile
        35                  40

```
<210> SEQ ID NO 65
<211> LENGTH: 39
<212> TYPE: PRT
<213> ORGANISM: Artificial
<220> FEATURE:
<223> OTHER INFORMATION: HAX9 39 mer fragment L-form

<400> SEQUENCE: 65
```

Ser Arg Glu Glu Ala Asn Trp Asp Gly Tyr Lys Arg Glu Met Ser His
1               5                   10                  15

Arg Ser Arg Phe Trp Asp Ala Thr His Leu Ser Arg Pro Arg Arg Pro
            20                  25                  30

Ala Asn Ser Gly Asp Pro Asn
        35

```
<210> SEQ ID NO 66
<211> LENGTH: 44
```

<212> TYPE: PRT
<213> ORGANISM: Artificial
<220> FEATURE:
<223> OTHER INFORMATION: HAX35 44 mer fragment L-form

<400> SEQUENCE: 66

Glu Trp Tyr Ser Trp Lys Arg Ser Ser Lys Ser Thr Gly Leu Gly Asp
1               5                   10                  15

Thr Ala Thr Arg Glu Gly Cys Gly Pro Ser Gln Ser Asp Gly Cys Pro
            20                  25                  30

Tyr Asn Gly Arg Leu Thr Thr Val Lys Pro Arg Lys
        35                  40

<210> SEQ ID NO 67
<211> LENGTH: 44
<212> TYPE: PRT
<213> ORGANISM: Artificial
<220> FEATURE:
<223> OTHER INFORMATION: HAX40 44 mer fragment L-form

<400> SEQUENCE: 67

Arg Glu Phe Ala Glu Arg Arg Leu Trp Gly Cys Asp Asp Leu Ser Trp
1               5                   10                  15

Arg Leu Asp Ala Glu Gly Cys Gly Pro Thr Pro Ser Asn Arg Ala Val
            20                  25                  30

Lys His Arg Lys Pro Arg Pro Arg Ser Pro Ala Leu
        35                  40

<210> SEQ ID NO 68
<211> LENGTH: 44
<212> TYPE: PRT
<213> ORGANISM: Artificial
<220> FEATURE:
<223> OTHER INFORMATION: HAX42 44 mer fragment L-form

<400> SEQUENCE: 68

Ser Asp His Ala Leu Gly Thr Asn Leu Arg Ser Asp Asn Ala Lys Glu
1               5                   10                  15

Pro Gly Asp Tyr Asn Cys Cys Gly Asn Gly Asn Ser Thr Gly Arg Lys
            20                  25                  30

Val Phe Asn Arg Arg Pro Ser Ala Ile Pro Thr
        35                  40

<210> SEQ ID NO 69
<211> LENGTH: 44
<212> TYPE: PRT
<213> ORGANISM: Artificial
<220> FEATURE:
<223> OTHER INFORMATION: HCA3 44 mer fragment L-form

<400> SEQUENCE: 69

Arg His Ile Ser Glu Tyr Ser Phe Ala Asn Ser His Leu Met Gly Gly
1               5                   10                  15

Glu Ser Lys Arg Lys Gly Cys Gly Ile Asn Gly Ser Phe Ser Pro Thr
            20                  25                  30

Cys Pro Arg Ser Pro Thr Pro Ala Phe Arg Arg Thr
        35                  40

<210> SEQ ID NO 70
<211> LENGTH: 38
<212> TYPE: PRT
<213> ORGANISM: Artificial
<220> FEATURE:

<223> OTHER INFORMATION: H40 38 mer fragment L-form

<400> SEQUENCE: 70

Ser Arg Glu Ser Gly Met Trp Gly Ser Trp Trp Arg Gly His Arg Leu
1               5                   10                  15

Asn Ser Thr Gly Gly Asn Ala Asn Met Asn Ala Ser Leu Pro Pro Asp
            20                  25                  30

Pro Pro Val Ser Thr Pro
        35

<210> SEQ ID NO 71
<211> LENGTH: 39
<212> TYPE: PRT
<213> ORGANISM: Artificial
<220> FEATURE:
<223> OTHER INFORMATION: PAX2 39 mer fragment L-form

<400> SEQUENCE: 71

Ser Thr Pro Pro Ser Arg Glu Ala Tyr Ser Arg Pro Tyr Ser Val Asp
1               5                   10                  15

Ser Asp Ser Asp Thr Asn Ala Lys His Ser Ser His Asn Arg Arg Leu
            20                  25                  30

Arg Thr Arg Ser Arg Pro Asn
        35

<210> SEQ ID NO 72
<211> LENGTH: 11
<212> TYPE: PRT
<213> ORGANISM: Artificial
<220> FEATURE:
<223> OTHER INFORMATION: binding 11 mer fragment L-form
<220> FEATURE:
<221> NAME/KEY: MISC_FEATURE
<222> LOCATION: (1)..(1)
<223> OTHER INFORMATION: "X=S or T"
<220> FEATURE:
<221> NAME/KEY: MISC_FEATURE
<222> LOCATION: (3)..(3)
<223> OTHER INFORMATION: "X= R or K"
<220> FEATURE:
<221> NAME/KEY: MISC_FEATURE
<222> LOCATION: (4)..(4)
<223> OTHER INFORMATION: "X= K or R"
<220> FEATURE:
<221> NAME/KEY: MISC_FEATURE
<222> LOCATION: (6)..(6)
<223> OTHER INFORMATION: "X= S or L"
<220> FEATURE:
<221> NAME/KEY: MISC_FEATURE
<222> LOCATION: (7)..(7)
<223> OTHER INFORMATION: "X= R,I,V or S "
<220> FEATURE:
<221> NAME/KEY: MISC_FEATURE
<222> LOCATION: (8)..(8)
<223> OTHER INFORMATION: "X= S, Y, F, or H "
<220> FEATURE:
<221> NAME/KEY: MISC_FEATURE
<222> LOCATION: (10)..(10)
<223> OTHER INFORMATION: "X=F, H or R "

<400> SEQUENCE: 72

Xaa Thr Xaa Xaa Ser Xaa Xaa Xaa Asn Xaa Arg
1               5                   10

<210> SEQ ID NO 73
<211> LENGTH: 8
<212> TYPE: PRT
<213> ORGANISM: Artificial
<220> FEATURE:

```
<223> OTHER INFORMATION: binding 8 mer fragment L-form
<220> FEATURE:
<221> NAME/KEY: MISC_FEATURE
<222> LOCATION: (2)..(2)
<223> OTHER INFORMATION: "X=S,A or G"
<220> FEATURE:
<221> NAME/KEY: MISC_FEATURE
<222> LOCATION: (4)..(4)
<223> OTHER INFORMATION: "X=V or Q"
<220> FEATURE:
<221> NAME/KEY: MISC_FEATURE
<222> LOCATION: (7)..(7)
<223> OTHER INFORMATION: "X = P, G or S"
<220> FEATURE:
<221> NAME/KEY: MISC_FEATURE
<222> LOCATION: (8)..(8)
<223> OTHER INFORMATION: "X =  W or Y"

<400> SEQUENCE: 73

Asp Xaa Asp Xaa Arg Arg Xaa Xaa
1               5

<210> SEQ ID NO 74
<211> LENGTH: 10
<212> TYPE: PRT
<213> ORGANISM: Artificial
<220> FEATURE:
<223> OTHER INFORMATION: binding 10 mer fragment L-form
<220> FEATURE:
<221> NAME/KEY: MISC_FEATURE
<222> LOCATION: (7)..(7)
<223> OTHER INFORMATION: "X = A or F"
<220> FEATURE:
<221> NAME/KEY: MISC_FEATURE
<222> LOCATION: (8)..(8)
<223> OTHER INFORMATION: "X = R or H"

<400> SEQUENCE: 74

Val Arg Ser Gly Cys Gly Xaa Xaa Ser Ser
1               5                   10

<210> SEQ ID NO 75
<211> LENGTH: 11
<212> TYPE: PRT
<213> ORGANISM: Artificial
<220> FEATURE:
<223> OTHER INFORMATION: binding 11 mer fragment L-form

<400> SEQUENCE: 75

Asn Thr Arg Lys Ser Ser Arg Ser Asn Pro Arg
1               5                   10

<210> SEQ ID NO 76
<211> LENGTH: 11
<212> TYPE: PRT
<213> ORGANISM: Artificial
<220> FEATURE:
<223> OTHER INFORMATION: binding 11 mer fragment L-form

<400> SEQUENCE: 76

Ser Thr Lys Arg Ser Leu Ile Tyr Asn His Arg
1               5                   10

<210> SEQ ID NO 77
<211> LENGTH: 10
<212> TYPE: PRT
<213> ORGANISM: Artificial
<220> FEATURE:
<223> OTHER INFORMATION: binding 10 mer fragment L-form

<400> SEQUENCE: 77
```

```
Ser Thr Gly Arg Lys Val Phe Asn Arg Arg
1               5                   10

<210> SEQ ID NO 78
<211> LENGTH: 11
<212> TYPE: PRT
<213> ORGANISM: Artificial
<220> FEATURE:
<223> OTHER INFORMATION: binding 11 mer fragment L-form

<400> SEQUENCE: 78

Thr Asn Ala Lys His Ser Ser His Asn Arg Arg
1               5                   10

<210> SEQ ID NO 79
<211> LENGTH: 8
<212> TYPE: PRT
<213> ORGANISM: Artificial
<220> FEATURE:
<223> OTHER INFORMATION: binding 8 mer fragment L-form

<400> SEQUENCE: 79

Asp Ser Asp Val Arg Arg Pro Trp
1               5

<210> SEQ ID NO 80
<211> LENGTH: 8
<212> TYPE: PRT
<213> ORGANISM: Artificial
<220> FEATURE:
<223> OTHER INFORMATION: binding 8 mer fragment L-form

<400> SEQUENCE: 80

Ala Ala Asp Gln Arg Arg Gly Trp
1               5

<210> SEQ ID NO 81
<211> LENGTH: 8
<212> TYPE: PRT
<213> ORGANISM: Artificial
<220> FEATURE:
<223> OTHER INFORMATION: binding 8 mer fragment L-form

<400> SEQUENCE: 81

Asp Gly Arg Gly Gly Arg Ser Tyr
1               5

<210> SEQ ID NO 82
<211> LENGTH: 4
<212> TYPE: PRT
<213> ORGANISM: Artificial
<220> FEATURE:
<223> OTHER INFORMATION: binding 4 mer fragment L-form

<400> SEQUENCE: 82

Arg Val Arg Ser
1

<210> SEQ ID NO 83
<211> LENGTH: 12
<212> TYPE: PRT
<213> ORGANISM: Artificial
<220> FEATURE:
<223> OTHER INFORMATION: binding 12 mer fragment L-form

<400> SEQUENCE: 83
```

```
-continued

Ser Val Arg Ser Gly Cys Gly Phe Arg Gly Ser Ser
1               5                   10

<210> SEQ ID NO 84
<211> LENGTH: 11
<212> TYPE: PRT
<213> ORGANISM: Artificial
<220> FEATURE:
<223> OTHER INFORMATION: binding 11 mer fragment L-form

<400> SEQUENCE: 84

Ser Val Arg Gly Gly Cys Gly Ala His Ser Ser
1               5                   10
```